(12) United States Patent
Orion

(10) Patent No.: US 11,291,565 B1
(45) Date of Patent: Apr. 5, 2022

(54) ASYMMETRIC EXTERNAL SUPPORT FOR STABILIZING A VEIN GRAFT USED IN A CORONARY ARTERIAL BYPASS GRAFT (CABG) PROCEDURE, AND APPLICATIONS THEREOF

(71) Applicant: Vascular Graft Solutions Ltd., Tel-Aviv (IL)

(72) Inventor: Eyal Orion, Ramat Efal (IL)

(73) Assignee: Vascular Graft Solutions Ltd.

( * ) Notice: Subject to any disclaimer, the term of this patent is extended or adjusted under 35 U.S.C. 154(b) by 0 days.

(21) Appl. No.: 17/237,096

(22) Filed: Apr. 22, 2021

(51) Int. Cl.
| | |
|---|---|
| *A61F 2/86* | (2013.01) |
| *A61F 2/07* | (2013.01) |
| *A61F 2/06* | (2013.01) |
| A61B 17/00 | (2006.01) |
| A61B 17/11 | (2006.01) |

(52) U.S. Cl.
CPC ............... *A61F 2/86* (2013.01); *A61F 2/07* (2013.01); A61B 2017/00862 (2013.01); A61B 2017/1107 (2013.01); A61B 2017/1132 (2013.01); A61F 2/064 (2013.01); A61F 2002/075 (2013.01); A61F 2220/0075 (2013.01)

(58) Field of Classification Search
CPC ...... A61F 2/82; A61F 2/86; A61F 2/88; A61F 2/885; A61F 2/90; A61F 2/94; A61F 2/95; A61F 2/04; A61F 2/07; A61B 2017/00862; A61B 2017/1107; A61B 2017/1132
See application file for complete search history.

(56) References Cited

U.S. PATENT DOCUMENTS

| | | | |
|---|---|---|---|
| 6,251,135 B1 * | 6/2001 | Stinson | ..................... A61F 2/82 623/1.34 |
| 8,057,537 B2 | 11/2011 | Zilla et al. | |
| 8,172,746 B2 | 5/2012 | Zilla et al. | |
| 8,382,814 B2 | 2/2013 | Zilla et al. | |
| 8,734,503 B2 | 5/2014 | Orion et al. | |
| 8,747,451 B2 | 6/2014 | Zilla et al. | |
| 8,906,082 B2 | 12/2014 | Zilla et al. | |
| 9,265,632 B2 | 2/2016 | Orion et al. | |

(Continued)

*Primary Examiner* — Wade Miles
(74) *Attorney, Agent, or Firm* — Endurance Law Group PLC

(57) ABSTRACT

Asymmetric external support for stabilizing vein grafts used in coronary arterial bypass graft (CABG) procedures, and applications thereof. Includes: tubular wire braided mesh longitudinally extending proximally and distally, configured with non-paired elastic wires and paired plastically deformable wires. Elastic wires extend along support full length. Paired plastically deformable wires proximal ends are non-connected and open. Plastically deformable wires extend less than support full length, and are configured with inter-looped distal end portions (loops) proximally longitudinally offset from support distal end, and outwardly radially extending beyond support outer radius. Loops may be individually secured, via loop closure securing procedures. In CABG procedures, support externally covers vein grafts, whereby support distal portion (with longitudinally offset loops) is positionable at coronary artery anastomosis sites, and support proximal end is positionable at other anastomosis sites. Eliminates, or minimizes, plastically deformable wires from injuring heart or/and vascular tissue in vicinity of coronary artery anastomosis sites.

20 Claims, 15 Drawing Sheets

(56) References Cited

U.S. PATENT DOCUMENTS

| | | |
|---|---|---|
| 9,517,069 B2 | 12/2016 | Zilla et al. |
| 9,517,121 B2 | 12/2016 | Zilla et al. |
| 9,949,852 B2 | 4/2018 | Orion et al. |
| 10,595,868 B2 | 3/2020 | Zilla et al. |
| 2003/0212449 A1* | 11/2003 | Cox ........................ A61F 2/915 623/1.15 |
| 2010/0324651 A1* | 12/2010 | Holzer .................... A61F 2/958 623/1.15 |
| 2016/0045304 A1* | 2/2016 | Orion .................... A61B 17/11 623/1.13 |
| 2020/0093622 A1* | 3/2020 | Nolan ...................... A61F 2/95 |

* cited by examiner asymmetric external support 100 asymmetric external support 100 asymmetric external support 100 asymmetric external support 200 asymmetric external support 200 asymmetric external support 200 support *proximal* portion 100pp support *proximal* portion 200pp

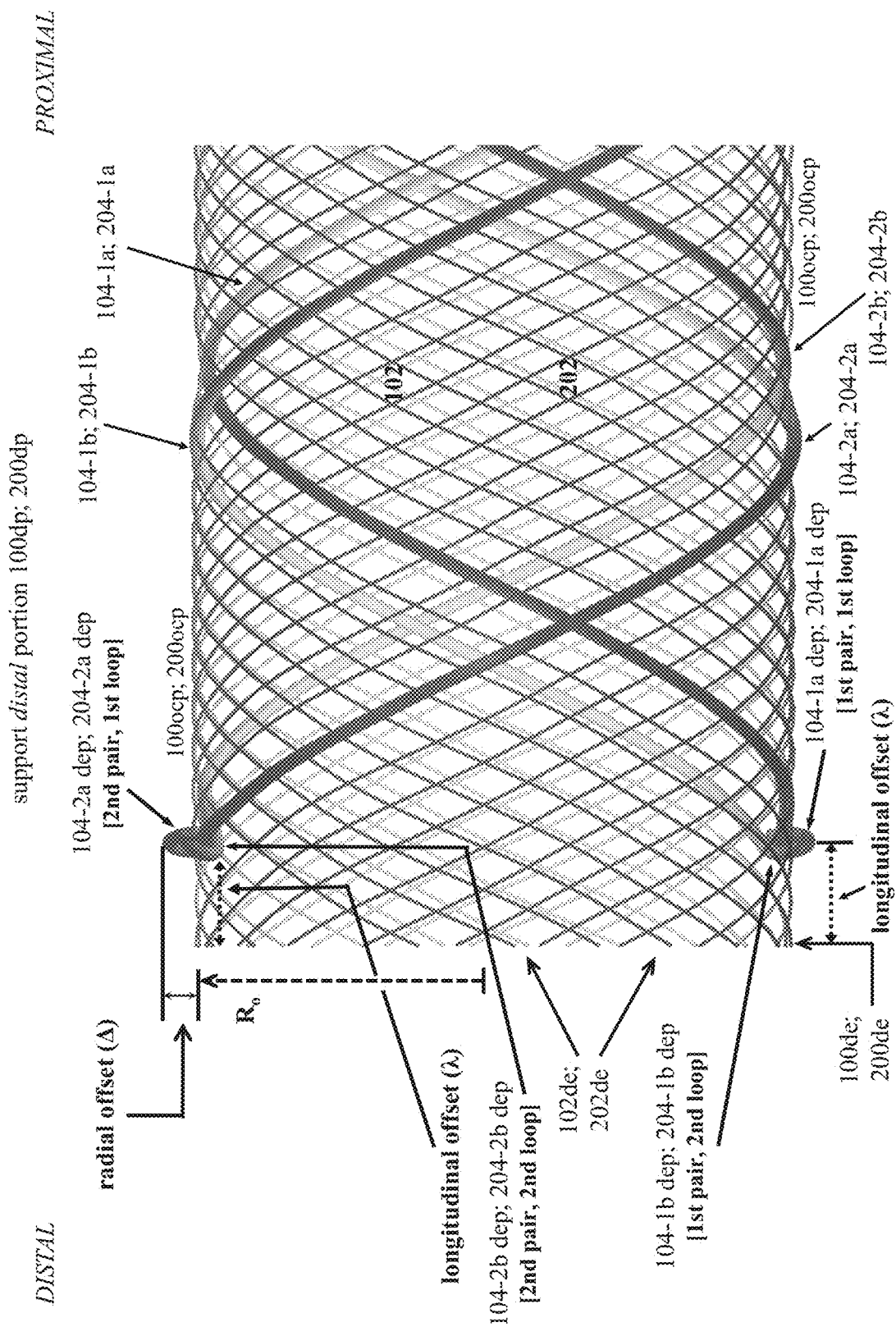

support *distal* portion 100dp; 200dp prototype asymmetric external support 120 support *distal* portion 120dp

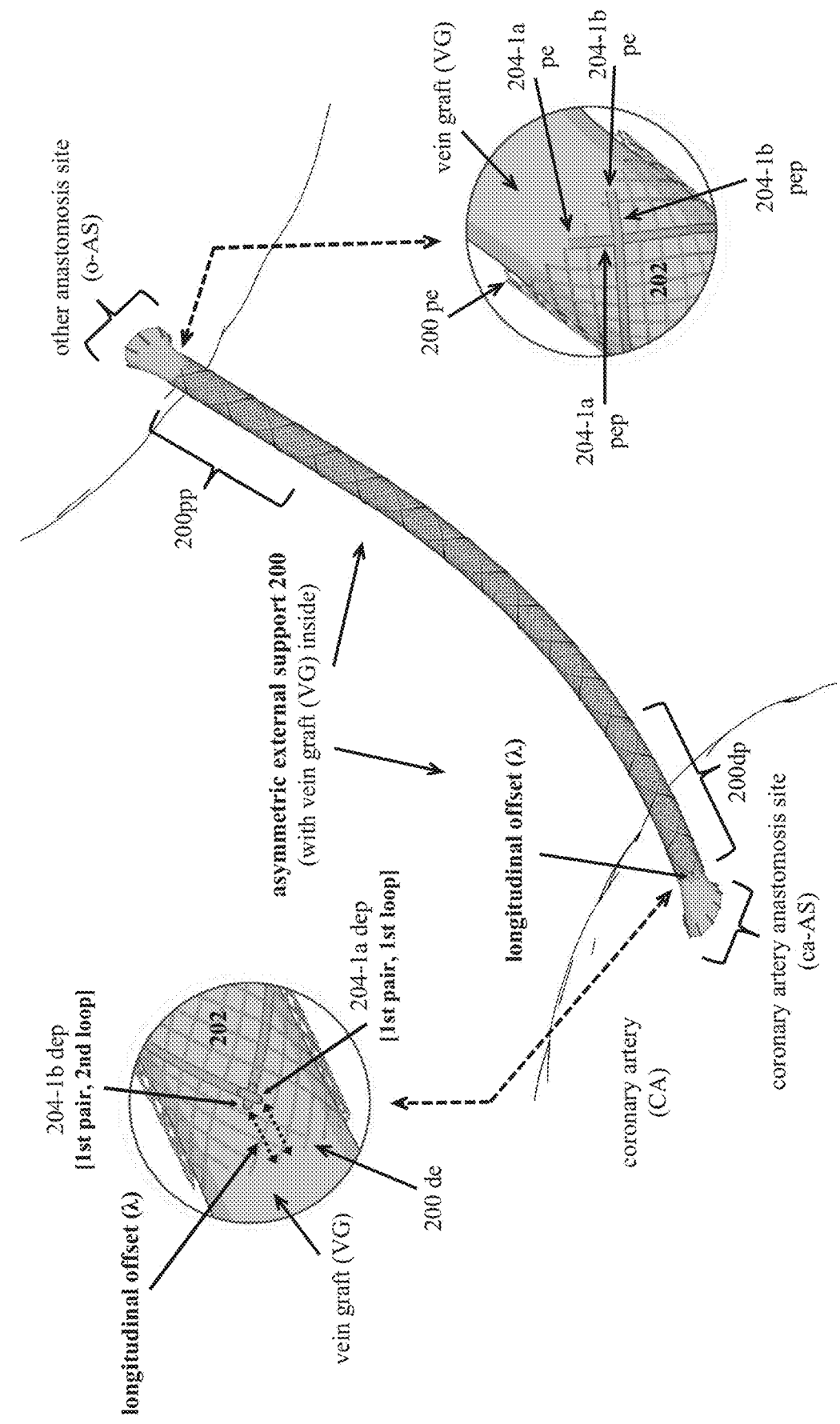
FIG. 8 asymmetric external support 200 in a CABG procedure

ASYMMETRIC EXTERNAL SUPPORT FOR STABILIZING A VEIN GRAFT USED IN A CORONARY ARTERIAL BYPASS GRAFT (CABG) PROCEDURE, AND APPLICATIONS THEREOF

FIELD OF THE INVENTION

The present invention relates to vascular implants that externally cover vein grafts used in coronary arterial bypass graft (CABG) procedures, and more particularly, to an asymmetric external support for stabilizing a vein graft used in a coronary arterial bypass graft (CABG) procedure, and applications thereof.

BACKGROUND OF THE INVENTION

Despite the proposed benefits of various types of arterial grafts, autologous saphenous vein grafts (SVGs) are still the most frequently used bypass conduits in coronary arterial bypass graft (CABG) procedures. Decades of extensive research have provided deep insights into the pathogenesis and natural history of arterial vein graft disease. However, until recently, these findings have not translated into effective therapies. Beginning several days after implantation of an arterial SVG, SVG disease is dominated by intimal hyperplasia which involves smooth muscle cell proliferation and migration to dysfunctional intima. High arterial pressures and circumferential wall stress, coupled with the development of lumen irregularities and abnormal flow patterns, are the main contributors to adverse structural remodeling and diffuse intimal hyperplasia that eventually predispose an arterial SVG to thrombosis and accelerated atherosclerosis. To date, only persistent use of statins and P-blockers have been shown to reduce to some extent intimal hyperplasia in arterial SVGs.

With a main objective of preventing, or at least reducing, adverse remodeling and disease development in arterial vein grafts used to replace or bypass diseased arteries that are subjected to arterial (high pressure/high flow) hemodynamics, vascular implant devices and techniques were conceived of and developed for external stenting of arterial vein grafts. Since Dr. Victor Parsonnet initially disclosed (in 1963) the technique of external stenting of arterial vein grafts with synthetic plastic vascular prostheses in an animal model, potential benefits of the technique have been extensively investigated in pre-clinical research. Devices and techniques for external stenting of arterial vein grafts used in human CABG procedures were developed by Zilla, et al. (for example, U.S. Pat. Nos. 8,057,537; 8,172,746; 8,382,814; 8,747,451; 8,906,082; 9,517,069; 9,517,121; and 10,595, 868). Unfortunately, clinical trials employing those external stenting devices and techniques provided disappointing results, with early SVG patency of 0-28% at 6-9 months.

Next generation biomechanically improved devices and techniques for external stenting of arterial vein grafts used in human CABG procedures were developed by Orion, et al. (for example, U.S. Pat. Nos. 8,734,503; 9,265,632; and 9,949,852). Recent clinical trials employing such devices and external stenting techniques have provided more promising results, with early SVG patency of 86-100%. Additional studies using intravascular ultrasound (IVUS) and optical coherence tomography (OCT) have offered profound insights into the biomechanical effects of external stenting, by demonstrating significant reductions in lumen irregularities, intimal hyperplasia, thrombus formation, and oscillatory shear stress in externally stented arterial SVGs at 1 year and 4.5 years after performing CABG.

Despite the above advancements, there is an on-going need for developing and implementing new and improved vascular implants and techniques for external stenting of arterial vein grafts used in CABG procedures.

SUMMARY OF THE INVENTION

The present invention relates to vascular implants that externally cover vein grafts used in coronary arterial bypass graft (CABG) procedures, and more particularly, to an asymmetric external support for stabilizing a vein graft used in a coronary arterial bypass graft (CABG) procedure, and applications thereof. Exemplary applications of the herein disclosed asymmetric external support are in methods for externally supporting and stabilizing a vein graft used in a coronary arterial bypass graft (CABG) procedure.

According to an aspect of some embodiments of the present invention, there is provided an asymmetric external support for stabilizing a vein graft used in a coronary arterial bypass graft procedure, the asymmetric external support comprising: a tubular wire mesh longitudinally extending proximally and distally with wire mesh proximal, middle, and distal portions, and, wire mesh proximal and distal ends, the wire mesh is configured with non-paired elastic wires and paired plastically deformable wires; the non-paired elastic wires longitudinally extend along full longitudinal length of the wire mesh, whereby proximal and distal ends of the elastic wires coincide with the wire mesh proximal and distal ends, respectively; the wire mesh proximal portion has the proximal ends of all the paired plastically deformable wires being non-connected and open; the wire mesh distal portion has the paired plastically deformable wires configured with inter-looped distal end portions, whereby each pair of the plastically deformable wires has a first wire with a first wire distal end portion formed as a first wire closed loop that is inter-looped with a second wire distal end portion formed as a second wire closed loop of a second wire; the paired plastically deformable wires longitudinally extend along less than the full longitudinal length of the wire mesh, whereby apexes of all the inter-looped distal end portions are proximally longitudinally offset from, and not coincident with, the wire mesh distal end; and wherein, in the coronary arterial bypass graft procedure, the asymmetric external support is externally applicable upon, to cover, the vein graft in a manner such that the wire mesh distal end is positionable at a coronary artery anastomosis site, and the wire mesh proximal end is positionable at an other anastomosis site.

In exemplary embodiments of the invention, the asymmetric external support (herein, for brevity, also referred to as 'the support') for stabilizing a vein graft used in a coronary arterial bypass graft (CABG) procedure, is in the form of a tubular wire braid or mesh (herein, for brevity, also referred to as 'the wire mesh') longitudinally extending proximally and distally along the full longitudinal length of the support. The support (wire mesh) has a proximal portion, a middle portion, a distal portion, a proximal end, and a distal end. The support (wire mesh) has an outer radius, and has an outer circumferential periphery that spans along, and parallel to, the full longitudinal length of the support (wire mesh). Such outer circumferential periphery corresponds to the (virtual or effective) circular (tubular) surface that surrounds (encircles, encompasses, bounds) the support (wire mesh) along, and parallel to, its full longitudinal length.

The support (wire mesh) is configured with non-paired elastic wires and paired plastically deformable wires. In exemplary embodiments, the exemplary asymmetric external support has an exemplary total number of 42 wires (or filaments), including an exemplary total number of 38 non-paired elastic wires (filaments), and an exemplary total number of 4 paired plastically deformable wires (filaments) corresponding to two pairs of two plastically deformable wires (filaments). The non-paired elastic wires longitudinally extend along the full longitudinal length of the support (wire mesh), whereby the proximal ends of the elastic wires coincide with the support (wire mesh) proximal end, and the distal ends of the elastic wires coincide with the support (wire mesh) distal end. The non-paired elastic wires circumferentially outwardly facing external surfaces (spanning along, and parallel to, the full longitudinal length of the support (wire mesh) coincide with, and 'physically' define, the support (wire mesh) outer circumferential periphery.

The support (wire mesh) proximal portion is configured with all the paired plastically deformable wires having proximal ends that are non-connected (i.e., not connected to, or looped (inter-looped) with, any other wire of the support (wire mesh)) and are open. In exemplary embodiments, the support (wire mesh) proximal portion is configured with all the paired plastically deformable wires having proximal ends that are coincident with the support (wire mesh) proximal end. Alternatively, in exemplary embodiments, the support (wire mesh) proximal portion is configured with not all (e.g., only one of, or even none of) the paired plastically deformable wires having proximal ends that are coincident with the support (wire mesh) proximal end. In exemplary embodiments, in the support (wire mesh) proximal portion, all of the paired plastically deformable wires have proximal end portions that do not cross over or under each other, whereby, in each pair of the plastically deformable wires, the proximal end portion of the first wire does not cross over or under the proximal end portion of the second wire. Alternatively, in exemplary embodiments, in the support (wire mesh) proximal portion, all of the paired plastically deformable wires have proximal end portions that cross over or under each other, whereby, in each pair of the plastically deformable wires, the proximal end portion of the first wire crosses over or under the proximal end portion of the second wire.

The asymmetric external support was developed in a 'customizable' manner, according to different particular scenarios, conditions, and parameters of different CABG procedures, and based on actual empirical (clinical) data and information obtained from performing CABG procedures using external supports on arterial vein grafts. Such customization was implemented in order to produce different possible embodiments/configurations of the support (wire mesh) distal portion wherein the paired plastically deformable wires are configured with pairs of inter-looped distal end portions (i.e., in each pair of the plastically deformable wires, a first wire has a distal end portion configured as a first loop, that is inter-looped with a second loop of a second wire distal end portion.

In different exemplary embodiments, the plastically deformable wires distal end portions (loops) exhibit different degrees of mobility (i.e., from relatively high mobility to relatively low mobility), or full immobility (i.e., being fixed). Since the support (wire mesh) distal portion consists of the non-paired elastic wires closely braided or meshed (intertwined, interwoven) with, and physically contacting, the paired plastically deformable wires, therefore, particular structural/mechanical configurations, along with mobility, or immobility, of the paired plastically deformable wires inter-looped distal end portions (loops) can, and are expected to, affect the structural/mechanical performance of immediately adjacent, and neighboring, non-paired elastic wires in the support (wire mesh) distal portion. Thus, particular structural/mechanical configurations, along with mobility, or immobility, of the paired plastically deformable wires inter-looped distal end portions (loops) are directly related to, and determine, structural/mechanical performance of the support (wire mesh) distal portion, in particular, and of the overall support (wire mesh), in general.

Customization of different possible embodiments/configurations of the asymmetric external support, in general, and of the support (wire mesh) distal portion, in particular, can translate into having support 'structural/mechanical' features exhibit different (favorable) performance characteristics during initial application and implantation (via an operator) of the support, and during the lifetime (in a patient) of the support. That, in turn, can translate into further improving SVG patency and safe use, as well as operator (e.g., surgeon) handling and manipulating characteristics, of the support for externally stenting an arterial vein graft used in a human CABG procedure.

In the support (wire mesh) distal portion, the paired plastically deformable wires are configured with inter-looped distal end portions (loops), whereby each pair of the plastically deformable wires has a first wire distal end portion formed as a first wire closed loop [1st loop] that is looped (i.e., inter-looped) with a second wire distal end portion formed as a second wire closed loop [2nd loop]. In such embodiments, each pair of the plastically deformable wires has a first wire whose distal end portion forms a first wire closed loop [1st loop] with a first wire loop end back-folded upon the first wire (so as to close the 1st loop), and has a second wire whose distal end portion forms a second wire closed loop [2nd loop] with a second wire loop end looped (inter-looped) through the first wire closed loop and back-folded upon the second wire (so as to close the 2nd loop).

In such embodiments, the 'back-fold' of each wire loop end upon its respective wire can have different particular configurations. In exemplary embodiments, the 'back-fold' of the wire loop end upon the wire is configured, whereby the ultimate end or tip (i.e., the utmost, farthest, or most distant part) of the wire loop end is aligned (so as to be co-axial/co-linear), and makes physical contact, with a particular segment or point along the remaining part of its respective wire. Alternatively, in exemplary embodiments, the 'back-fold' of the wire loop end upon the wire is configured, whereby the ultimate end or tip (i.e., the utmost, farthest, or most distant part) of the wire loop end crosses over or under, and onto its respective wire, in an 'x-like' transverse manner, so as to slightly extend past the wire, with a particular segment of that extended wire making physical contact with a particular segment or point along the remaining part of its respective wire.

Regarding mobility of the inter-looped distal end portions (loops), in exemplary embodiments, in the support (wire mesh) distal portion, in each pair of the plastically deformable wires, and in the inter-looped distal end portions, the two individual loops (i.e., the two individual looped distal end portions that are inter-looped with each other) are configured so as to be (longitudinally or/and radially) slidably movable relative to each other. In such embodiments, the loop (inter-looped distal end portion) of the first wire and the loop (inter-looped distal end portion) of the second wire, are (longitudinally or/and radially) slidably movable relative to each other. Equivalently stated, in each pair of the plastically deformable wires, the first wire distal end portion (formed as the first wire closed loop [1st loop]) and the second wire distal end portion (formed as the second wire closed loop [2nd loop]), that are inter-looped with each other, are configured so as to be (longitudinally or/and radially) slidably movable relative to each other. Such exemplary embodiments of the inter-looped distal end portions (loops) being slidably movable relative to each other require that, not both, but, at least one, of the two individual loops (i.e., at least one of the two individual looped distal end portions that are inter-looped with each other) in each pair of the plastically deformable wires is configured with a sufficiently large loop size that facilitates the (radial or/and longitudinal) slidable mobility of the two loops relative to each other. In exemplary embodiments, not one, but, both of the two individual loops in each pair of the plastically deformable wires are configured with a sufficiently large loop size that facilitates the slidable mobility of the two loops relative to each other.

Regarding immobility of the inter-looped distal end portions (loops), in exemplary embodiments, in the support (wire mesh) distal portion, in each pair of the plastically deformable wires, and in the inter-looped distal end portions, the two individual loops (i.e., the two individual looped distal end portions that are inter-looped with each other) are configured so as not to be slidably movable (i.e., they are immobile, or fixed in place) relative to each other. In such embodiments, the loop (inter-looped distal end portion) of the first wire and the loop (inter-looped distal end portion) of the second wire, are not (longitudinally or/and radially) slidably movable relative to each other, rather, the loops of the first and second wires are immobile, or fixed, relative to each other. Equivalently stated, in each pair of the plastically deformable wires, the first wire distal end portion (formed as the first wire closed loop [1st loop]) and the second wire distal end portion (formed as the second wire closed loop [2nd loop]), that are inter-looped with each other, are configured so as not to be slidably movable (i.e., they are immobile, or fixed in place) relative to each other. Such exemplary embodiments of the inter-looped distal end portions (loops) not being slidably movable (i.e., being immobile, fixed in place) relative to each other require that, not both, but, at least one, of the two individual loops (i.e., at least one of the two individual looped distal end portions that are inter-looped with each other) in each pair of the plastically deformable wires is configured with a sufficiently small loop size that fully prevents (radial or longitudinal) slidable mobility of the two loops relative to each other. In exemplary embodiments, not one, but, both of the two individual loops in each pair of the plastically deformable wires are configured with a sufficiently small loop size that fully prevents slidable mobility of the two loops relative to each other.

For the above described exemplary embodiments/configurations of the support (wire mesh) distal portion that exhibit different degrees of mobility (i.e., from relatively high mobility to relatively low mobility), or full immobility (i.e., being fixed), in the paired plastically deformable wires inter-looped distal end portions (loops), the loop size may be quantifiable and measurable, for example, in terms of the inner [circular or elliptical loop-shape] area of, and encompassed by, a single loop, which is then used for (custom) designing, and subsequently forming, the inter-looped distal end portions (loops) of the paired plastically deformable wires in the support (wire mesh) distal portion. Accordingly, for such exemplary embodiments, having the ability to control the loop size (i.e., inner [loop-shape] area of each loop), translates into having the ability to control the degree or extent of mobility, or immobility, provided to the paired plastically deformable wires inter-looped distal end portions (loops) in the support (wire mesh) distal portion. This, in turn, facilitates the asymmetric external support structural/mechanical features to exhibit different (favorable) 'customized' performance characteristics during initial application and implantation (via an operator) of the support, and during the lifetime (in a patient) of the support.

Exemplary embodiments of the herein disclosed asymmetric external support include securing (reinforcing) closure of the loops (loop closures). Such exemplary embodiments are based on using a loop closure securing (reinforcing) procedure, in particular, (i) a loop closure adhering procedure, or (ii) a loop closure heat treatment (e.g., welding, or soldering) procedure. In such exemplary embodiments, in the support (wire mesh) distal portion, in each inter-looped pair of the plastically deformable wires, each inter-looped distal end portion (loop) has a loop closure (i.e., the closure [closed part] of the loop) that is individually secured or reinforced, via use of a loop closure securing (reinforcing) procedure, in particular, above listed (i) or (ii). Moreover, each loop closure (the closure [closed part] of each loop of the two (inter-looped) loops in each inter-looped distal end portion) is individually secured or reinforced (via above (i) or (ii)), specifically at the particular location or point which the wire loop end is back-folded upon, and makes physical contact with, its respective wire.

Regarding (i) a loop closure adhering procedure, in exemplary embodiments, in the support (wire mesh) distal portion, in each inter-looped pair of the plastically deformable wires, each inter-looped distal end portion (loop) has a loop closure (i.e., the closure [closed part] of the loop) that may be individually secured or reinforced, via a loop closure adhering procedure, with adhesive material (e.g., medical grade glue or other adhesive type material) that is applied to the particular location or point at which the wire loop end is back-folded upon, and makes physical contact with, its respective wire. Regarding (ii) a loop closure heat treatment procedure, in exemplary embodiments, in the support (wire mesh) distal portion, in each inter-looped pair of the plastically deformable wires, each inter-looped distal end portion (loop) has a loop closure (i.e., the closure [closed part] of the loop) that may be individually secured or reinforced, via a loop closure heat treatment procedure, with welding or soldering applied to the particular location or point at which the wire loop end is back-folded upon, and makes physical contact with, its respective wire.

For the exemplary embodiments of (i) and (ii), the loop closure securing (reinforcing) procedure can be performed in order to produce different possible embodiments/configurations of the individually secured (reinforced) loop closures, such that in each pair of the plastically deformable wires, and in the inter-looped distal end portions thereof, the two closed loops with their two respective individually secured (reinforced) loop closures, can exhibit different degrees of relative mobility, or full immobility (i.e., being fixed), as described hereinabove. Implementation of the loop closure securing (reinforcing) procedure, to produce the indicated exemplary embodiments of the support (wire mesh), provides assurance that, during initial application and implantation of the support, and during the lifetime of the support in a patient, each closed loop with its individually secured (reinforced) loop closure (exhibiting either relative mobility, or full immobility), will not loosen, become unlooped, and open up.

The asymmetric external support was designed, and constructed, wherein the support (wire mesh) distal portion is configured with the paired plastically deformable wires longitudinally extending along less than the full longitudinal length of the support (wire mesh), whereby the apexes (i.e., the midpoints of the arched parts) of all the looped distal end portions (loops) are proximally longitudinally offset from, and not coincident with, the support (wire mesh) distal end. In exemplary embodiments, the support (wire mesh) proximal portion is configured with all the paired plastically deformable wires having proximal ends that are coincident with the support (wire mesh) proximal end. Alternatively, in exemplary embodiments, the support (wire mesh) proximal portion is configured with not all (e.g., only one of, or even none of) the paired plastically deformable wires having proximal ends that are coincident with the support (wire mesh) proximal end. In exemplary embodiments, the proximal longitudinal offset of the apex (midpoint of the arched part) of each looped (inter-looped) distal end portion (loop) of each plastically deformable wire from the (ultimate) distal end of the support (wire mesh), has a magnitude in a range of between 0.2 mm and 1.5 mm.

The asymmetric external support was designed, and constructed, wherein the support (wire mesh) distal portion has all the paired plastically deformable wires configured such that the first and second wire closed loops of the inter-looped distal end portions radially extend beyond the outer radius of the support (wire mesh). In such configurations, the apexes (midpoints of the arched parts) of all the looped (inter-looped) distal end portions (loops) are outwardly radially offset from, and not coincident with, the outer circumferential periphery of the support (wire mesh). In the support (wire mesh) distal portion, such radial extension beyond the outer radius of the support (wire mesh), and outwardly radial offset from, and non-coincidence with, the support (wire mesh) outer circumferential periphery, corresponds to the plastically deformable wires inter-looped distal end portions (loops) projecting (protruding, jutting, extending, sticking) out or outwardly from the outer radius of the support (wire mesh), whereby the apexes (midpoints of the arched parts) of all the looped distal end portions (loops) project (protrude, jut, extend, stick) out or outwardly from the outer circumferential periphery of the support (wire mesh). In exemplary embodiments, the outward radial offset of the apex (midpoint of the arched part) of each looped distal end portion of each plastically deformable wire out or outwardly from the outer circumferential periphery of the support (wire mesh), has a magnitude in a range of between 0.2 mm and 1.5 mm.

Regarding the support (wire mesh) middle portion, in contrast to the above described longitudinal and radial asymmetric aspects of the asymmetric external support (wire mesh) opposing proximal and distal portions, and of the paired plastically deformable wires therein, within the support (wire mesh) middle portion, the structural (geometrical and mechanical) features, properties, and characteristics of the non-paired elastic wires are spatially, longitudinally and radially symmetric and uniform, and, the structural (geometrical and mechanical) features, properties, and characteristics of the paired plastically deformable wires are spatially, longitudinally and radially symmetric and uniform.

Based on the numerous structural (geometrical and mechanical) aspects of the herein disclosed asymmetric external support, the asymmetric external support is spatially, 'longitudinally and radially' asymmetric (i.e., lacks symmetry) with respect to the opposing proximal and distal portions, and the respective opposing proximal and distal ends therein. Specifically, in the herein disclosed asymmetric external support, particular structural (geometrical and mechanical) features, properties, and characteristics are spatially, 'longitudinally and radially asymmetric' with respect to the opposing proximal and distal portions, and the respective opposing proximal and distal ends therein. More specifically, the support (wire mesh) distal portion, including the distal end therein, exhibits, and is characterized by, particular structural (geometrical and mechanical) features, properties, and characteristics that are asymmetric relative to, and substantially different from, the particular structural (geometrical and mechanical) features, properties, and characteristics exhibited by, and characterizing, the support (wire mesh) proximal portion, including the proximal end therein.

A first asymmetric feature is that in the support (wire mesh) distal portion, all paired plastically deformable wires are configured with looped distal end portions having closed ends, and in the support (wire mesh) proximal portion, all paired plastically deformable wires are configured with non-looped, non-connected proximal end portions having open ends. Thus, while the support (wire mesh) distal portion is configured with looped pairs of plastically deformable wires having closed ends, the support (wire mesh) proximal portion is configured with non-looped, non-connected pairs of plastically deformable wires having open ends.

A second asymmetric feature is that the paired plastically deformable wires longitudinally extend along less than the full longitudinal length of the support (wire mesh), whereby the apexes (midpoints of the arched parts) of all the looped distal end portions are proximally longitudinally offset from, and not coincident with, the (ultimate) distal end of the support (wire mesh). In exemplary embodiments, the proximal ends of all the paired plastically deformable wires are coincident with the (ultimate) proximal end of the support (wire mesh). Thus, in such exemplary embodiments, while the support (wire mesh) distal end is not coincident with the longitudinally offset apexes of all the looped distal end portions of the paired plastically deformable wires, the support (wire mesh) proximal end is coincident with the proximal ends of all the paired plastically deformable wires.

A third asymmetric feature is that in the support (wire mesh) distal portion, all the paired plastically deformable wires are configured with the looped distal end portions (loops) radially extending beyond the outer radius of the support (wire mesh), whereby the apexes (midpoints of the arched parts) of all the looped distal end portions (loops) are outwardly radially offset from, and not coincident with, the outer circumferential periphery of the support (wire mesh). Thus, while the outer circumferential periphery of the support (wire mesh) distal portion is not coincident with the radially offset apexes of all the looped distal end portions of the paired plastically deformable wires, the outer circumferential periphery of the support (wire mesh) proximal portion is coincident with the proximal ends of all the paired plastically deformable wires.

With respect to application of the herein disclosed asymmetric external support, in a coronary arterial bypass graft (CABG) procedure, the asymmetric external support is externally applicable upon, to cover, a vein graft in a manner such that the support (wire mesh) distal portion (with distal end therein) is positionable at a coronary artery anastomosis site, and the support (wire mesh) proximal portion (with proximal end therein) is positionable at an other anastomosis site.

Positioning of the support (wire mesh) distal portion (with the support (wire mesh) distal end therein) at the coronary artery anastomosis site, facilitates exploitation of the above described asymmetric features of the asymmetric external support. Namely, according to such particular directional positioning, following the vein graft distal end being anastomized directly to the coronary artery, the apexes of all the looped distal end portions (loops), and therefore, the distal-most parts, of all the paired plastically deformable wires in the support (wire mesh) distal portion will be proximally longitudinally located away (by more than the loops apexes proximal longitudinal offset) from, and not coincident with, the coronary artery anastomosis site. This results in eliminating, or at least minimizing, possibility that the apexes (distal-most parts) of the paired plastically deformable wires looped distal end portions (loops) will injure (via pricking or piercing) heart or/and vascular tissue in the immediate vicinity of the coronary artery anastomosis site.

Positioning of the support (wire mesh) proximal portion (with the support (wire mesh) proximal end therein) at an other anastomosis site, facilitates subsequent anastomosis of the support (wire mesh) proximal end to that other anastomosis site. In a coronary arterial bypass graft (CABG) procedure, exemplary other anastomosis sites are: (1) the aorta (more than 90% of time); (2) another venous graft (e.g., an SVG) anastomized directly to the aorta; (3) an arterial graft (e.g., a radial artery graft) anastomized to a coronary artery and to the aorta; and (4) an internal mammary artery.

All technical or/and scientific words, terms, or/and phrases, used herein have the same or similar meaning as commonly understood by one of ordinary skill in the art to which the invention pertains, unless otherwise specifically defined or stated herein. Exemplary embodiments of the herein disclosed invention are exemplary and illustrative only, and are not intended to be necessarily limiting.

BRIEF DESCRIPTION OF THE SEVERAL VIEWS OF THE DRAWINGS

Exemplary embodiments of the present invention are herein described, by way of example only, with reference to the accompanying drawings. With specific reference now to the drawings in detail, it is stressed that the particulars shown are by way of example and for purposes of illustrative description of exemplary embodiments of the present invention. In this regard, the description taken together with the accompanying drawings make apparent to those skilled in the art how exemplary embodiments of the present invention may be practiced.

In the drawings:

FIGS. 4A, 4B, and 4C are schematic close-up top, side, and perspective views, respectively, of an exemplary embodiment of the distal portion of the asymmetric external support (of FIGS. 1A, 1B, 1C, and 2A, 2B, 2C), highlighting the paired plastically deformable wires (longitudinally and radially offset) inter-looped distal end portions (loops), in accordance with some embodiments of the invention;

FIG. 8 is a schematic diagram of an exemplary embodiment of application of the asymmetric external support (of FIGS. 2A, 2B, 2C), in a CABG procedure, highlighting particular directional positioning of an externally supported vein graft, with the support distal portion (with distal end therein) at a coronary artery anastomosis site, and the support proximal portion (with proximal end therein) at an other anastomosis site, in accordance with some embodiments of the invention.

DESCRIPTION OF SPECIFIC EMBODIMENTS OF THE INVENTION

Figure 1A:
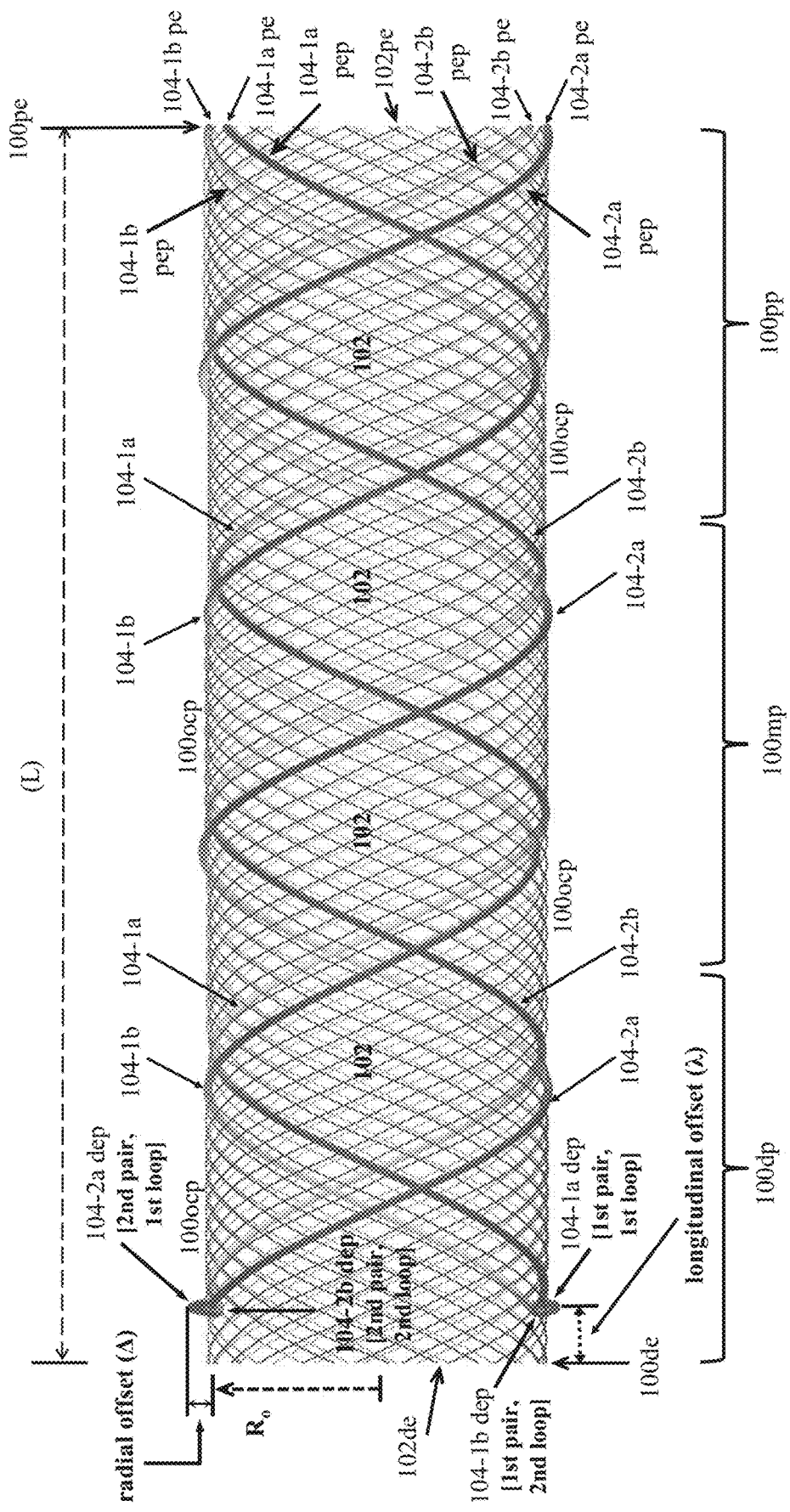
FIGS. 1A, 1B, and 1C are schematic top, side, and perspective views, respectively, of an exemplary embodiment of the asymmetric external support (as a tubular wire mesh), showing the paired plastically deformable wires (longitudinally and radially offset) inter-looped distal end portions (loops), and proximal non-connected open ends, with wire proximal end portions not crossing over or under each other, in accordance with some embodiments of the invention.

The present invention relates to an asymmetric external support for stabilizing a vein graft used in a coronary arterial bypass graft (CABG) procedure, and applications thereof. Exemplary applications of the herein disclosed asymmetric external support are in methods for externally supporting and stabilizing a vein graft used in a coronary arterial bypass graft (CABG) procedure.

With an important objective of improving early SVG patency of externally stented arterial vein grafts used in human CABG procedures, Orion, et al. developed biomechanically improved external supports and techniques employing such supports, as disclosed, for example, in U.S. Pat. Nos. 8,734,503; 9,265,632; and 9,949,852. As disclosed therein, those improved external supports, for example, in the form of tubular braided wire meshes, are fixedly displaceable relative to a longitudinal axis of the support, by plastically (i.e., not elastically) deforming the external support relative to the longitudinal axis. Plastically deforming the external support relative to the longitudinal axis is effected by (an operator, such as a surgeon) plastically stretching or compressing the external support along the longitudinal axis or/and by plastically bending the external support in a direction transverse to the longitudinal axis, with no, or minimal, (elastic) springback of the external support, such that the external support substantially maintains its new (plastically deformed) shape relative to the longitudinal axis. In such external supports, the tubular wire mesh attains its unique property of plastic deformability by including in its mesh structure at least one plastically deformable wire (or fiber), typically, a plurality of plastically deformable wires (fibers), extending along its longitudinal axis, while the remaining wires (fibers) of the tubular wire mesh are elastically deformable.

With another important objective of improving safe use of the implanted external supports, Orion, et al. (as cited above) additionally disclosed that in the improved external supports the tubular wire mesh may be constructed with one or more of the plastically deformable wires having an end portion that is blunted, for example, via heat treatment (e.g., welding, soldering), so as to reduce possibility of the wire mesh end portion injuring (via pricking or piercing) heart or/and vascular tissue. For the same objective, Orion, et al. also described embodiments of the external support wherein the tubular wire mesh is constructed with the end portions of two or more plastically deformable wires being looped together and attached (e.g., via welding, soldering) to the wire mesh, particularly, at the (ultimate) very end or edge of the external support.

Clinical trials based on using the above disclosed external supports and techniques achieved relatively high early SVG patency of 86-100%. Nevertheless, despite such relatively high SVG patency, the present inventor wanted to further improve SVG patency and safe use, as well as operator (e.g., surgeon) handling and manipulating characteristics, of external supports for externally stenting arterial vein grafts used in human CABG procedures.

As disclosed herein, the present inventor developed new embodiments/configurations of an external support, herein, referred to as an asymmetric external support, for stabilizing a vein graft used in a coronary arterial bypass graft (CABG) procedure, and applications thereof. The herein disclosed asymmetric external support is designed, and constructed, in a 'customizable' manner, according to different possible embodiments/configurations of the support that translates into facilitating support 'structural' features to exhibit different (favorable) performance characteristics during initial application and implantation (via an operator) of the support, and during the lifetime (in a patient) of the support. That, in turn, translates into further improving SVG patency and safe use, as well as operator (e.g., surgeon) handling and manipulating characteristics, of the support for externally stenting an arterial vein graft used in a human CABG procedure.

For purposes of further understanding exemplary embodiments of the present invention, in the following illustrative description thereof, reference is made to the figures. Throughout the following description and accompanying drawings, same reference numbers refer to same objects, components, elements, or features.

Additionally, throughout the description and accompanying drawings, physical orientational (location, position) and directional type terms "proximal", "proximally", "distal", and "distally", are used for indicating relative orientation (location, position) and direction of the stated or illustrated object, component, element, or structural feature of the herein disclosed asymmetric external support. For example, the term "proximal", as used herein, may refer to the location, position, or direction of the stated or illustrated object/s, component/s, element/s, or structural feature/s of the herein disclosed asymmetric external support that is/are 'nearer or closer to' (or towards) the operator or user (e.g., a surgeon) of the asymmetric external support. For example, the term "distal", as used herein, may refer to the location, position, or direction of the stated or illustrated object/s, component/s, element/s, or structural feature/s of the herein disclosed asymmetric external support that is/are 'farther' (or away) from the (e.g., surgeon) operator or user of the asymmetric external support. With respect to right and left sides of a printed page, or of a computer display, the terms "proximal" and "distal", as used herein, in a non-limiting manner, correspond to the right and left sides, respectively, thereof. It is to be understood that 'correspondingly opposite' terminology (i.e., "distal" instead of "proximal", and "proximal" instead of "distal") can be (consistently) used for fully and properly illustratively describing embodiments of the present invention.

Consistent with the preceding explained usage of the physical orientational and directional terms "proximal" and "distal", the term "longitudinally extending", as used herein, refers to the physical extension (spanning) of the stated or illustrated object, component, element, or structural feature along a longitudinal axis (e.g., a central longitudinal axis) that extends in (and along) the proximal direction and in (and along) the distal direction.

Asymmetric External Support

The herein disclosed asymmetric external support includes, or, alternatively, consists essentially of, or, alternatively, consists of, the following illustratively described components, and structural/functional features thereof.

The term "elastic wires", as used herein, refers to wires (or filaments) which exhibit, and are characterizable by, the property, condition, and phenomenon of elasticity. Such wires are elastically deformable, whereby after being (elastically) deformed, the wires return to their original shape and size. Such elastic wires will deform when forces are applied on them, and return to their initial shape and size when the forces are removed.

The term "plastically deformable wires", as used herein, refers to wires (or filaments) which exhibit, and are characterizable by, the property, condition, and phenomenon of plasticity. Such wires are plastically deformable, whereby after being (plastically) deformed, the wires do not return to their original shape and size. Such plastically deformable wires will permanently (non-reversibly or irreversibly) deform when forces applied on them are removed.

Figure 1B:
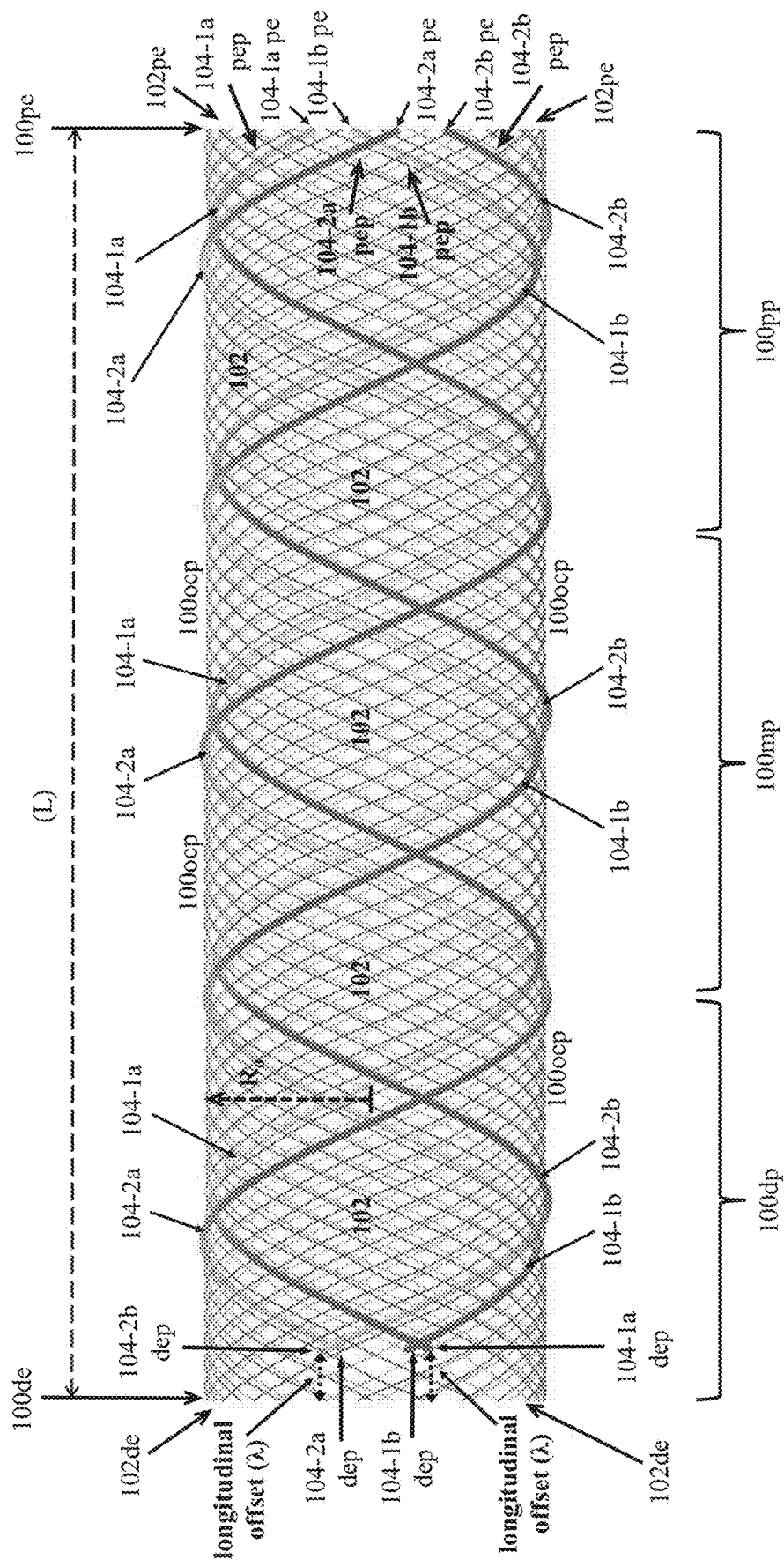
Figure 1C:
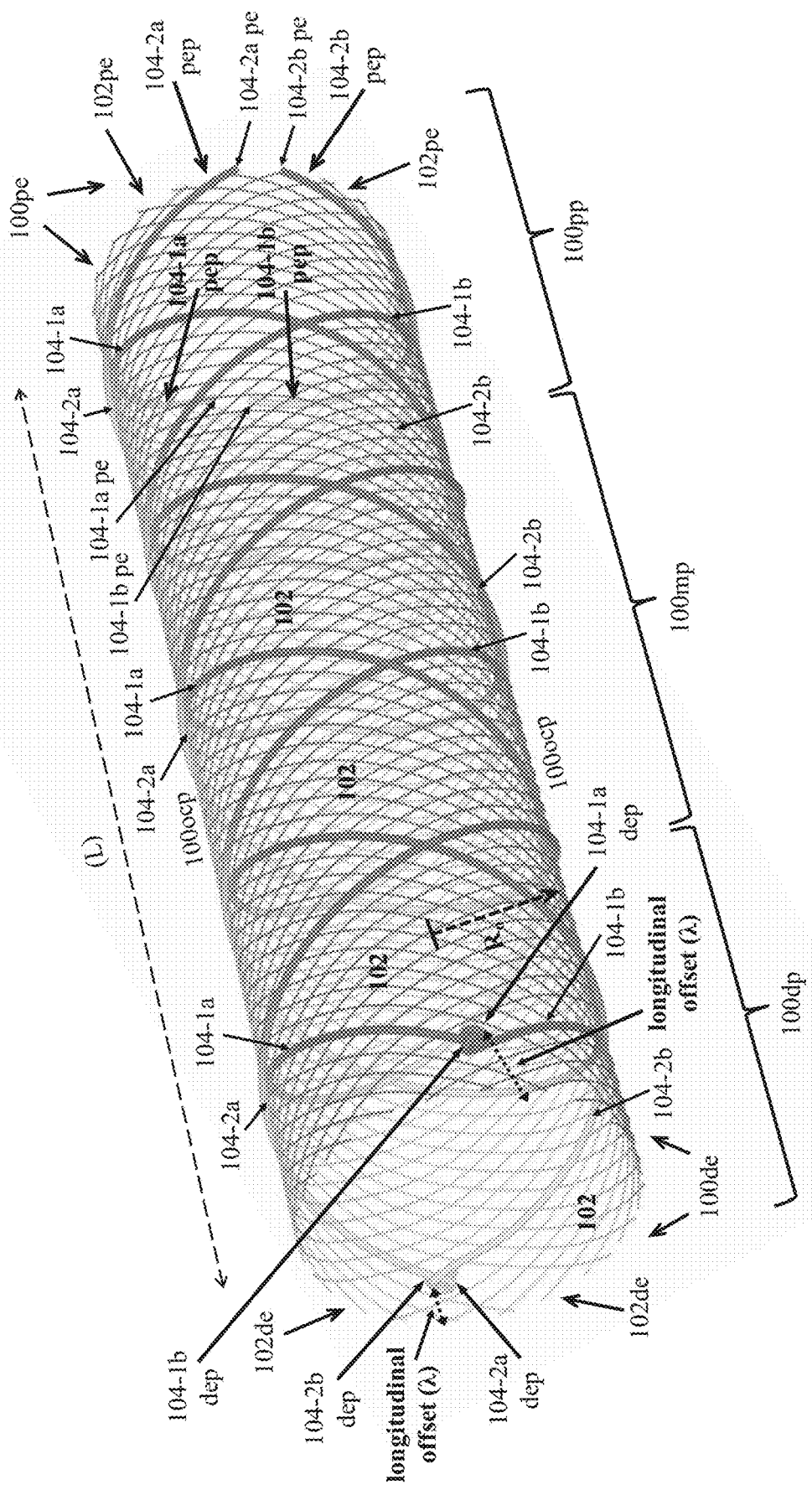
Figure 2A:
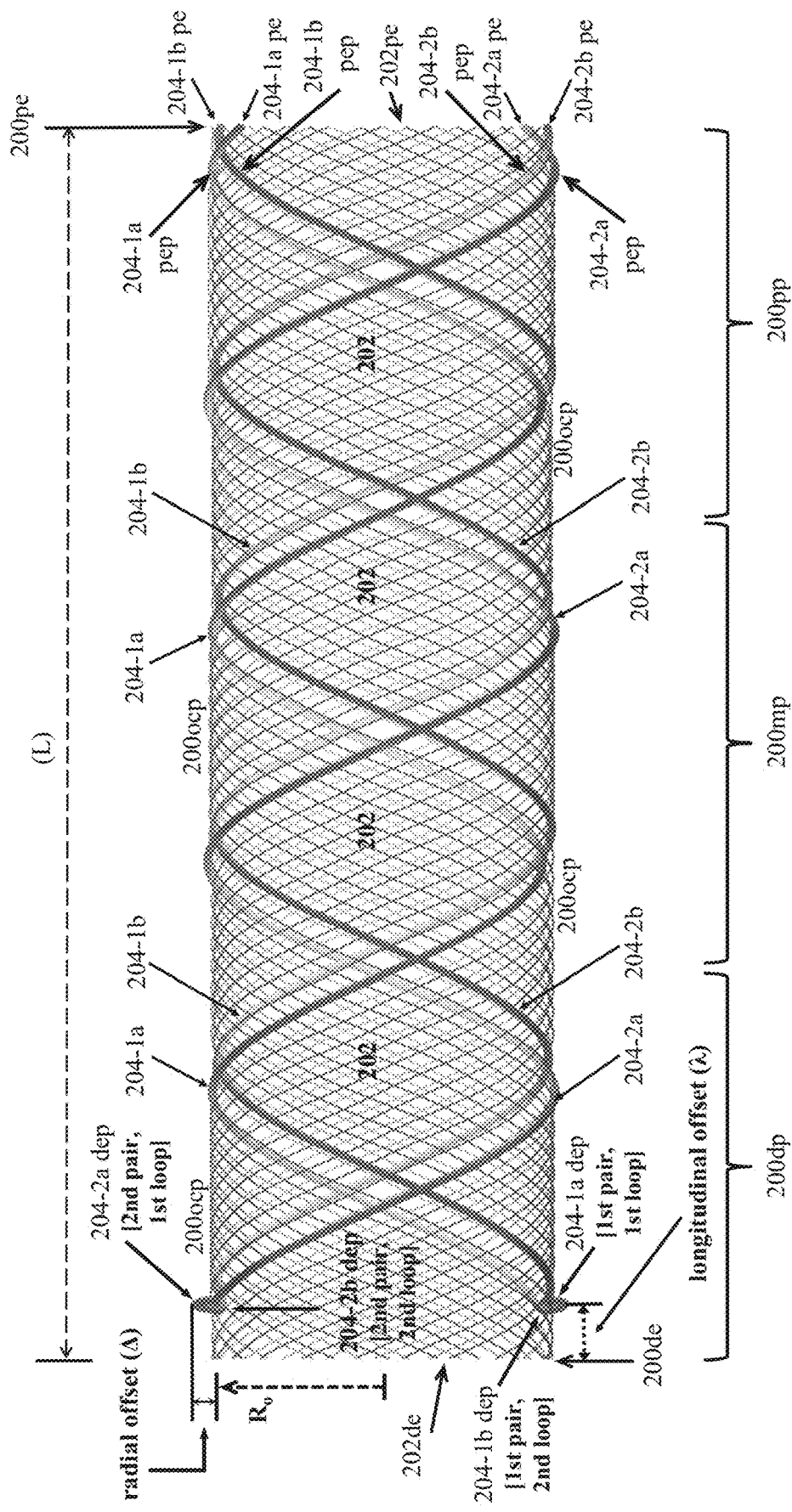
FIGS. 2A, 2B, and 2C are schematic top, side, and perspective views, respectively, of another exemplary embodiment of the asymmetric external support (as a tubular wire mesh), showing the paired plastically deformable wires (longitudinally and radially offset) inter-looped distal end portions (loops), and proximal non-connected open ends, with wire proximal end portions crossing over or under each other, in accordance with some embodiments of the invention.
Figure 2B:
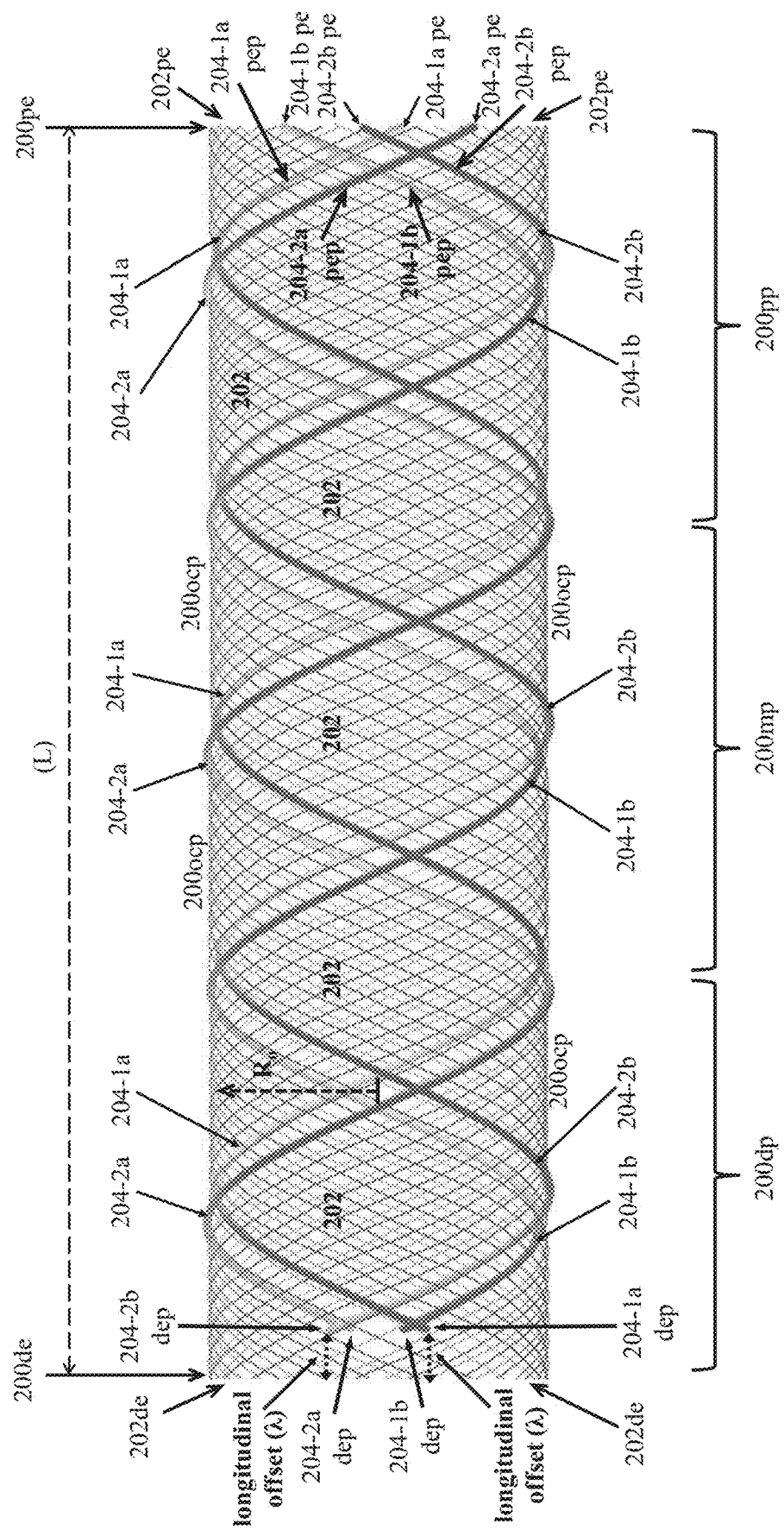
Figure 2C:
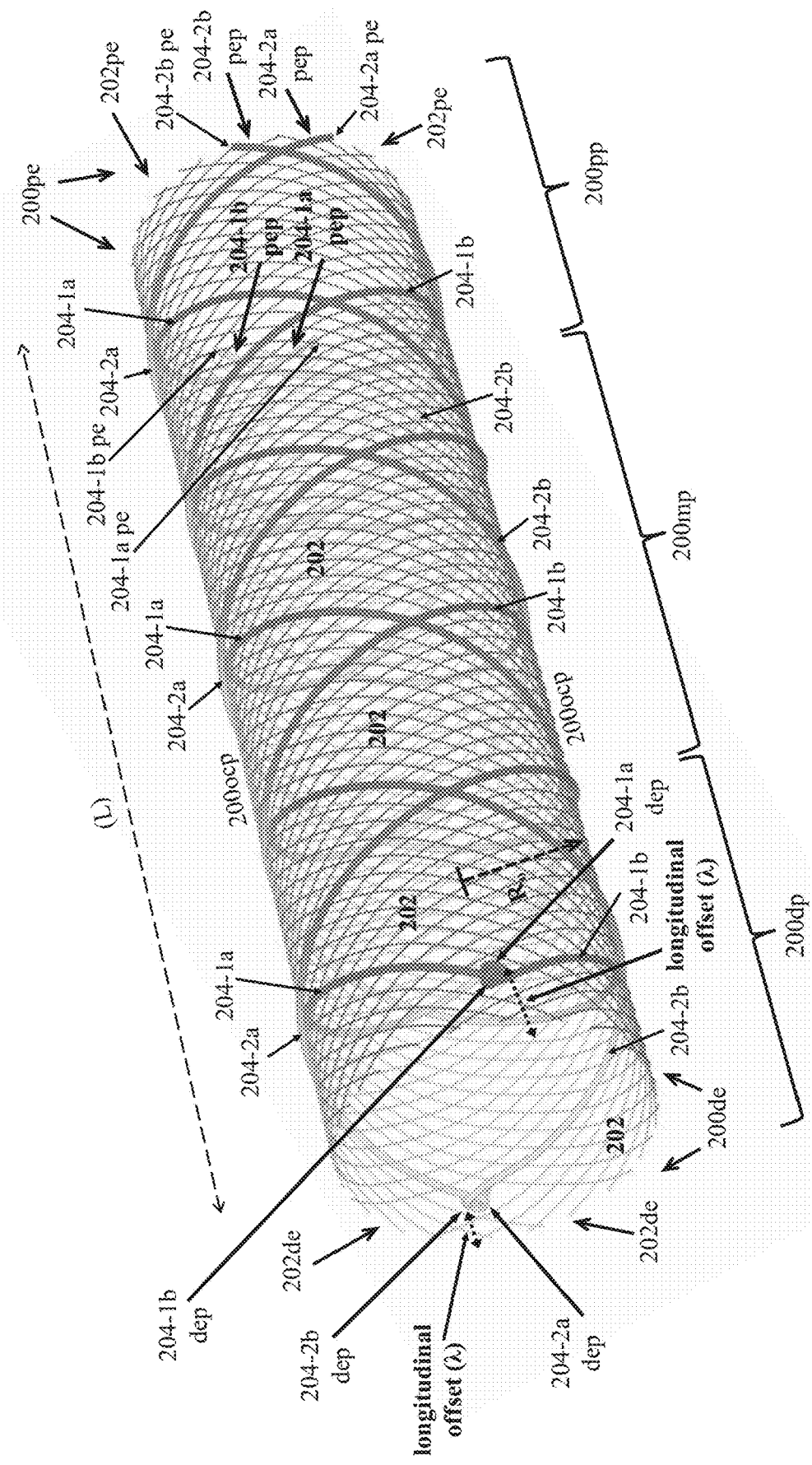

Referring now to the drawings, FIGS. 1A, 1B, and 1C are schematic top, side, and perspective views, respectively, of an exemplary embodiment of the asymmetric external support [indicated as, and referred to by, reference number 100], in the form of a tubular wire braid or mesh, for stabilizing a vein graft used in a coronary arterial bypass graft (CABG) procedure. FIGS. 1A, 1B, and 1C show the paired plastically deformable wires (longitudinally and radially offset) interlooped distal end portions (loops), and the paired plastically deformable wires proximal non-connected open ends, with the plastically deformable wires proximal end portions not crossing over or under each other. FIGS. 2A, 2B, and 2C are schematic top, side, and perspective views, respectively, of another exemplary embodiment of the asymmetric external support [indicated as, and referred to by, reference number 200], in the form of a tubular wire braid or mesh, for stabilizing a vein graft used in a coronary arterial bypass graft (CABG) procedure. FIGS. 2A, 2B, and 2C show the paired plastically deformable wires (longitudinally and radially offset) inter-looped distal end portions (loops), and the paired plastically deformable wires proximal non-connected open ends, with the plastically deformable wires proximal end portions crossing over or under each other.

Exemplary asymmetric external support 200 shown in FIGS. 2A, 2B, and 2C has all the same structural features, characteristics, and properties as exemplary asymmetric external support 100 shown in FIGS. 1A, 1B, and 1C, except for the particular configuration of the paired plastically deformable wires proximal end portions. Namely, as shown in FIGS. 1A, 1B, and 1C, exemplary external support 100 proximal portion is configured with all of the plastically deformable wires proximal end portions not crossing over or under each other, whereas, as shown in FIGS. 2A, 2B, and 2C, exemplary external support 200 proximal portion is configured with all of the plastically deformable wires proximal end portions crossing over or under each other.

Figure 3A:
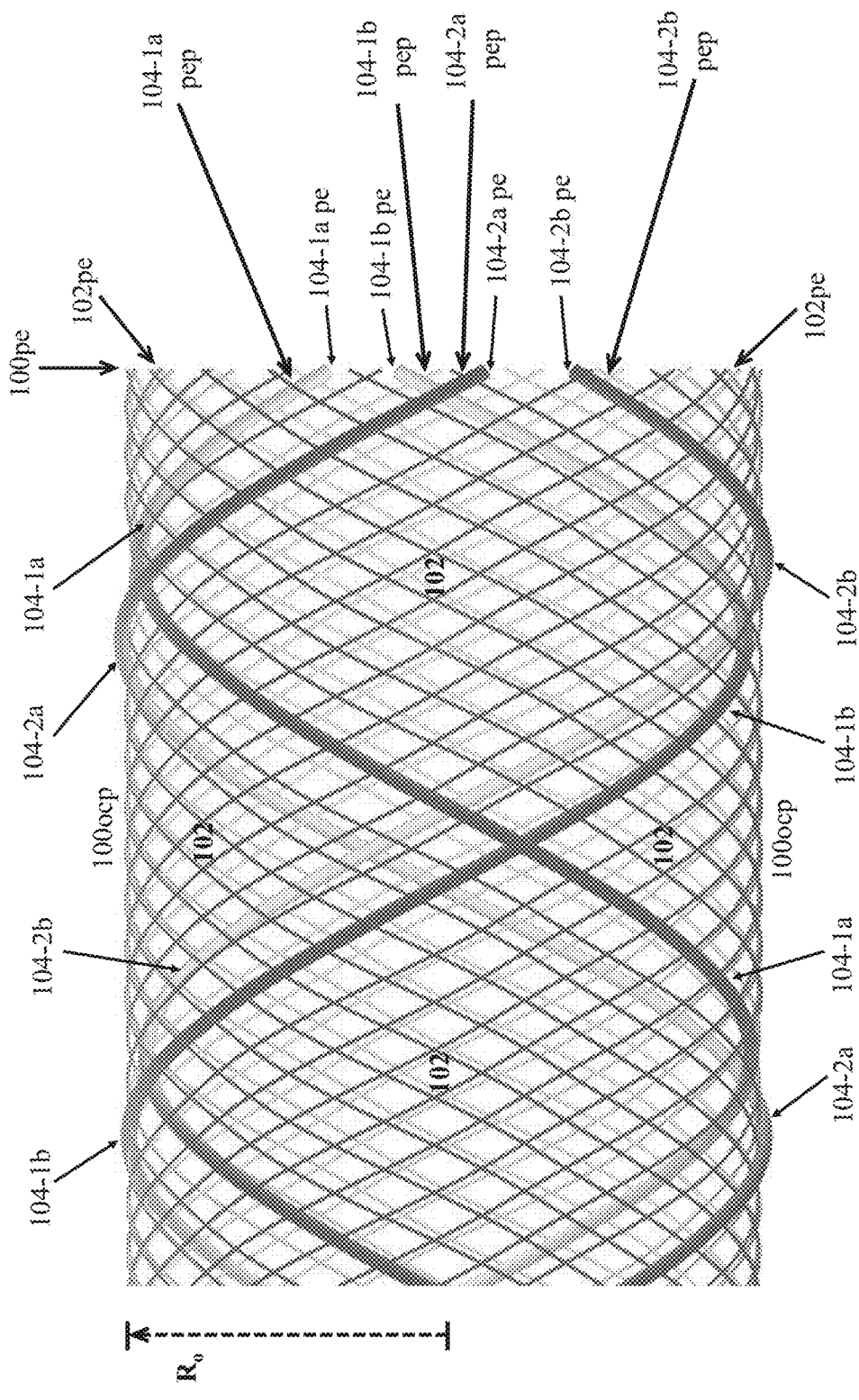
FIG. 3A is a schematic close-up side view of an exemplary embodiment of the proximal portion of the asymmetric external support (of FIGS. 1A, 1B, 1C), highlighting the paired plastically deformable wires proximal non-connected open ends (coincident with the asymmetric external support proximal end), with wire proximal end portions not crossing over or under each other, in accordance with some embodiments of the invention.
Figure 3B:
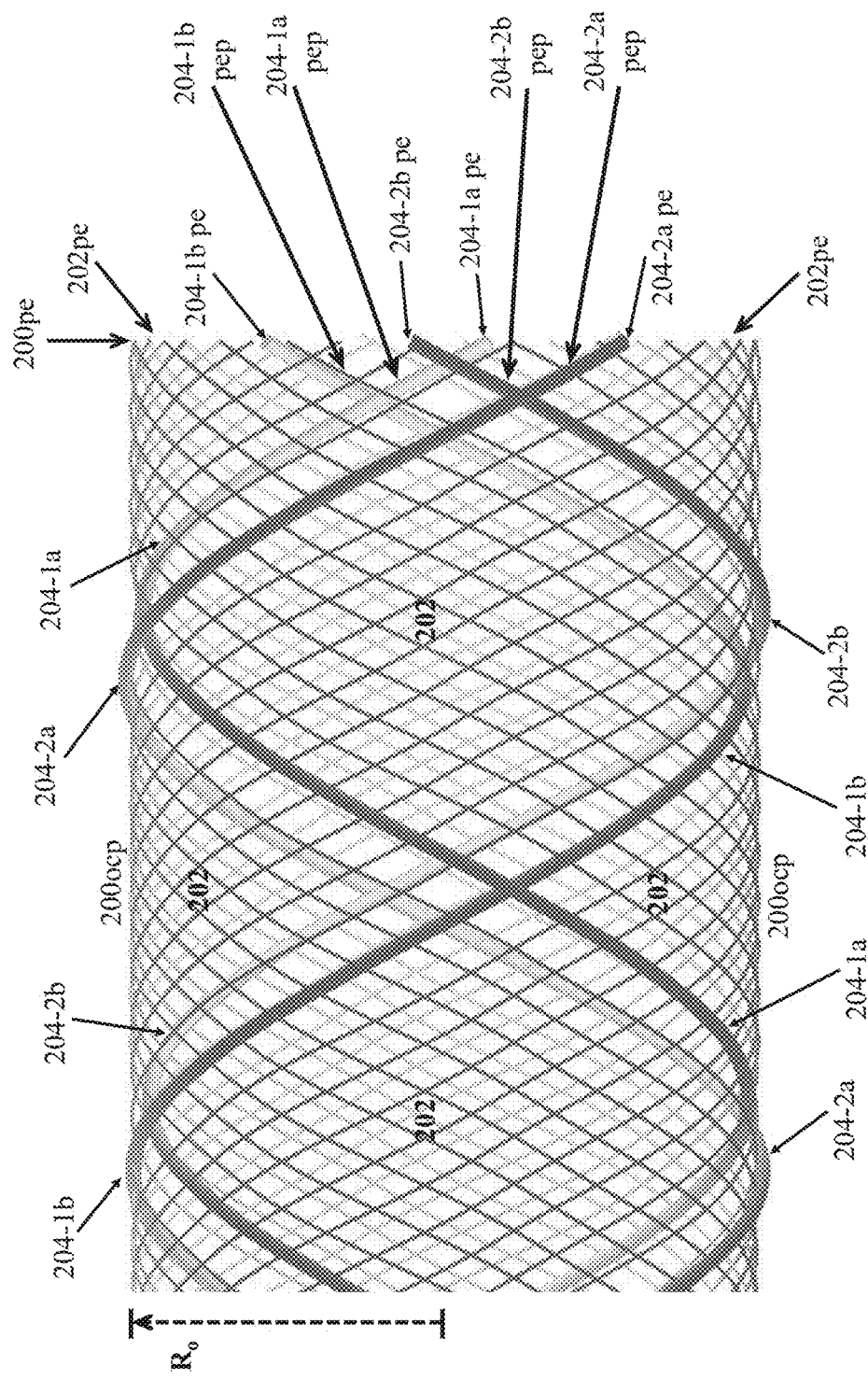
FIG. 3B is a schematic close-up side view of an exemplary embodiment of the proximal portion of the asymmetric external support (of FIGS. 2A, 2B, 2C), highlighting the paired plastically deformable wires proximal non-connected open ends (coincident with the asymmetric external support proximal end), with wire proximal end portions crossing over or under each other, in accordance with some embodiments of the invention.

FIG. 3A is a schematic close-up side view of an exemplary embodiment of the proximal portion of the asymmetric external support (100 of FIGS. 1A, 1B, 1C), highlighting the paired plastically deformable wires proximal non-connected open ends (coincident with the asymmetric external support proximal end), with the plastically deformable wires proximal end portions not crossing over or under each other. FIG. 3B is a schematic close-up side view of an exemplary embodiment of the proximal portion of the asymmetric external support (200 of FIGS. 2A, 2B, 2C), highlighting the paired plastically deformable wires proximal non-connected open ends (coincident with the asymmetric external support proximal end), with the plastically deformable wires proximal end portions crossing over or under each other.

Figure 4B:
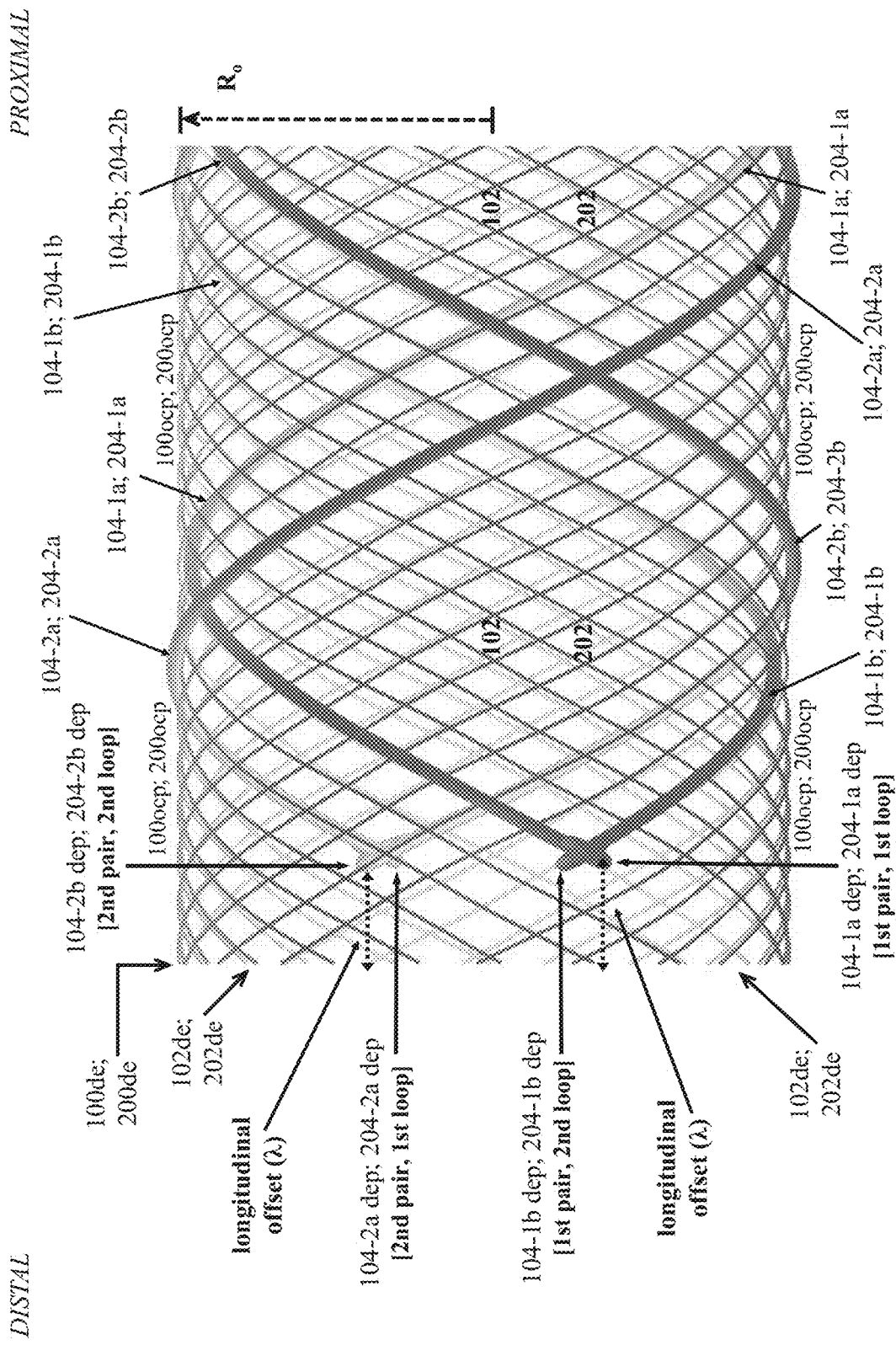
Figure 4C:
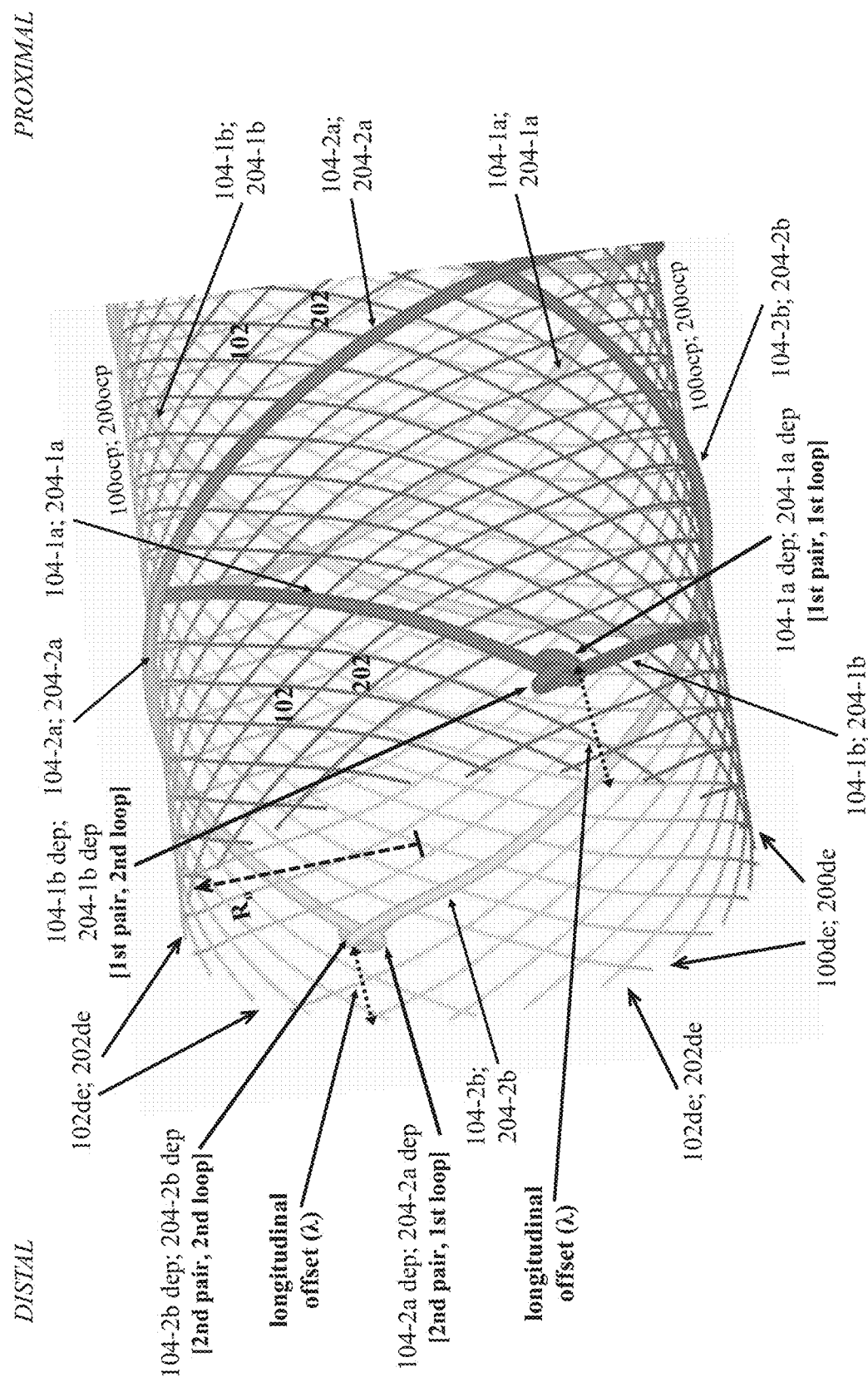

FIGS. 4A, 4B, and 4C are schematic close-up top, side, and perspective views, respectively, of an exemplary embodiment of the distal portion of the asymmetric external support (100 of FIGS. 1A, 1B, 1C; 200 of FIGS. 2A, 2B, 2C), highlighting the paired plastically deformable wires (longitudinally and radially offset) inter-looped distal end portions (loops), whereby apexes (midpoints of the arched parts) thereof are: (i) proximally longitudinally offset from, and not coincident with, the asymmetric external support distal end; and (ii) outwardly radially offset from, and not coincident with, the asymmetric external support outer circumferential periphery.

Figure 5:
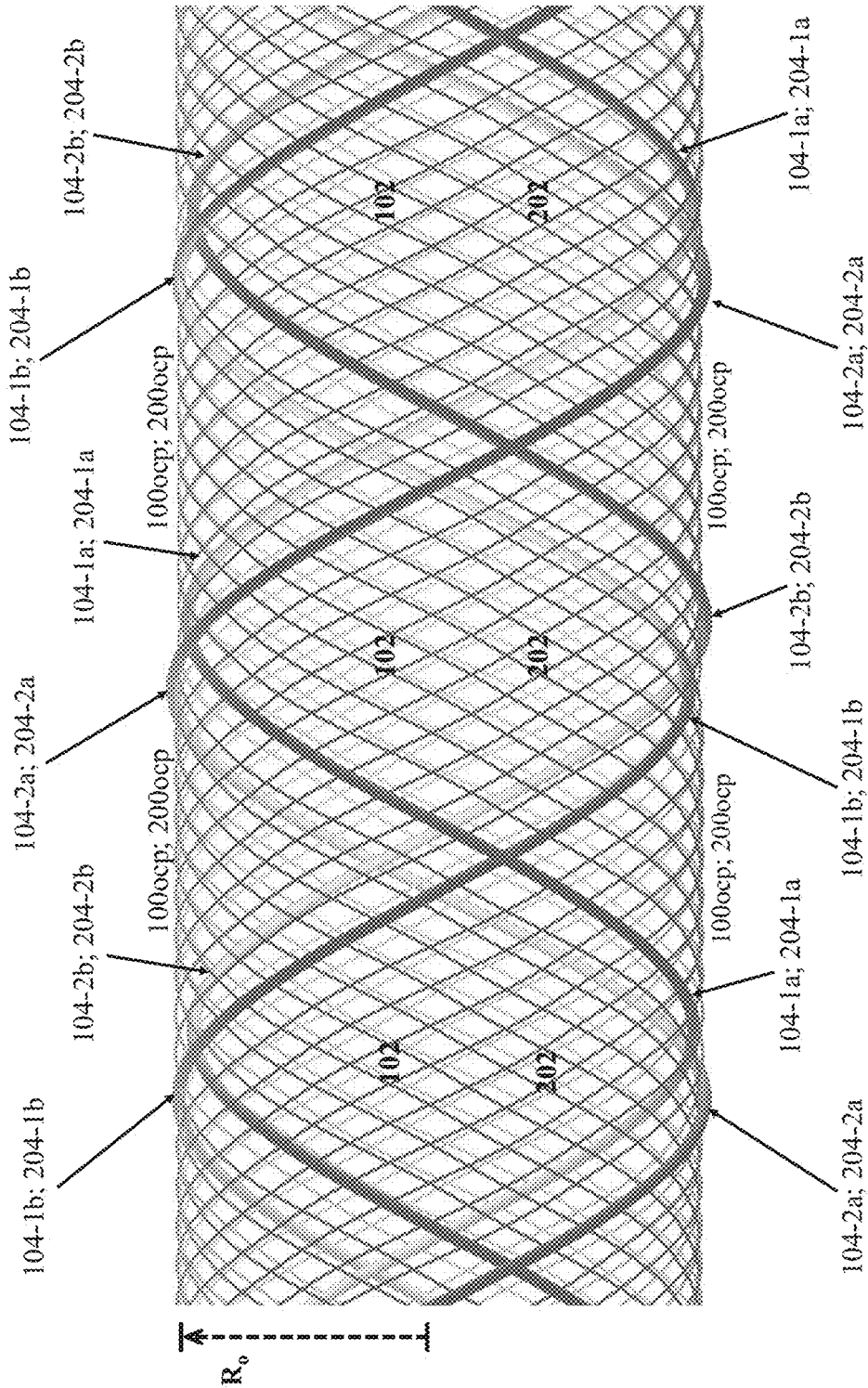
FIG. 5 is a schematic close-up side view of an exemplary embodiment of the middle portion of the asymmetric external support (of FIGS. 1A, 1B, 1C and 2A, 2B, 2C), highlighting the spatially, longitudinally and radially symmetric and uniform tubular wire mesh configuration of non-paired elastic wires and paired plastically deformable wires, in accordance with some embodiments of the invention.

FIG. 5 is a schematic close-up side view of an exemplary embodiment of the middle portion of the asymmetric external support (100 of FIGS. 1A, 1B, 1C; 200 of FIGS. 2A, 2B, 2C), highlighting the spatially, longitudinally and radially symmetric and uniform tubular wire mesh configuration of non-paired elastic wires and paired plastically deformable wires.

With reference to FIGS. 1 through 5, the exemplary asymmetric external supports (herein, for brevity, also referred to as the supports) 100 shown in FIGS. 1A, 1B, 1C; and 200 shown in FIGS. 2A, 2B, 2C, are in the forms of tubular wire braids or meshes (herein, also referred to as wire meshes 100 and 200, respectively) longitudinally extending proximally and distally along the full longitudinal length (L) of the support. The support (wire mesh) (100; 200) has a proximal portion (100pp; 200pp), a middle portion (100mp; 200mp), a distal portion (100dp; 200dp), a proximal end (100pe; 200pe), and a distal end (100de; 200de).

The support (wire mesh) (100; 200) has an outer radius ($R_o$), and has an outer circumferential periphery (or boundary) (100ocp; 200ocp) that spans along, and parallel to, the full longitudinal length (L) of the support (wire mesh) (100; 200). The outer circumferential periphery (100ocp; 200ocp) corresponds to the (virtual or effective) circular (tubular) surface that surrounds (encircles, encompasses, bounds) the support (wire mesh) (100; 200) along, and parallel to, its full longitudinal length (L). The outer circumferential periphery (100ocp; 200ocp) is formed by the (virtual or effective) circumferential lines (i.e., perimeters, circular boundaries) that encircle the support (wire mesh) (100; 200) and longitudinally span (sweep) proximally and distally along, and parallel to, the full longitudinal length (L) of the support (wire mesh) (100; 200).

The support (wire mesh) (100; 200) is configured with non-paired elastic wires (102; 202) and paired plastically deformable wires (104; 204). In exemplary embodiments, each support (wire mesh) (100; 200) has an exemplary total number of 42 wires (or filaments), including an exemplary total number of 38 non-paired elastic wires (filaments) (102; 202), and an exemplary total number of 4 paired plastically deformable wires (filaments) (104; 204) corresponding to two pairs of two plastically deformable wires (filaments).

In exemplary asymmetric external support (wire mesh) 100, the first pair of plastically deformable wires is indicated as, and referenced by, reference number 104-1, which includes a first pair, first plastically deformable wire 104-1a, and a first pair, second plastically deformable wire 104-1b. The second pair of plastically deformable wires is indicated as, and referenced by, reference number 104-2, which includes a second pair, first plastically deformable wire 104-2a and a second pair, second plastically deformable wire 104-2b.

In exemplary asymmetric external support (wire mesh) 200, the first pair of plastically deformable wires is indicated as, and referenced by, reference number 204-1, which includes a first pair, first plastically deformable wire 204-1a, and a first pair, second plastically deformable wire 204-1b. The second pair of plastically deformable wires is indicated as, and referenced by, reference number 204-2, which includes a second pair, first plastically deformable wire 204-2a and a second pair, second plastically deformable wire 204-2b.

The non-paired elastic wires (102; 202) longitudinally extend along the full longitudinal length (L) of the support (wire mesh) (100; 200), whereby the proximal ends (102pe; 202pe) of the elastic wires (102, 202) coincide with the support (wire mesh) proximal end (100pe; 200pe), and the distal ends (102de; 202de) of the elastic wires (102; 202) coincide with the support (wire mesh) distal end (100de; 200de). The non-paired elastic wires (102; 202) circumferentially outwardly facing external surfaces (spanning along, and parallel to, the full longitudinal length (L) of the support (wire mesh) (100; 200)) coincide with, and 'physically' define, the support (wire mesh) outer circumferential periphery (100ocp; 200ocp).

Support (Wire Mesh) Proximal Portion, and the Plastically Deformable Wires Therein The support (wire mesh) proximal portion (100pp; 200pp) is configured with all the paired plastically deformable wires (104; 204) having proximal ends (104-1a pe, 104-1b pe, 104-2a pe, 104-2b pe; 204-1a pe, 204-1b pe, 204-2a pe, 204-2b pe) that are non-connected (i.e., not connected to, or looped (inter-looped) with, any other wire of the support (wire mesh)) and are open.

In exemplary embodiments, the support (wire mesh) proximal portion (100pp; 200pp) is configured with all the paired plastically deformable wires (104; 204) having proximal ends (104-1a pe, 104-1b pe, 104-2a pe, 104-2b pe;

204-1*a* pe, 204-1*b* pe, 204-2*a* pe, 204-2*b* pe) that are coincident with the support (wire mesh) proximal end (100*pe*; 200*pe*). Alternatively, in exemplary embodiments, the support (wire mesh) proximal portion (100*pp*; 200*pp*) is configured with not all (e.g., only one of, or even none of) the paired plastically deformable wires (104; 204) having proximal ends that are coincident with the support (wire mesh) proximal end (100*pe*; 200*pe*).

In exemplary embodiments, as shown in FIGS. 1A, 1B, 1C, and 3A, in the support (wire mesh) proximal portion (100*pp*), all of the paired plastically deformable wires (104) have proximal end portions (104-1*a* pep, 104-1*b* pep, 104-2*a* pep, 104-2*b* pep) that do not cross over or under each other, whereby, in each pair (104-1, 104-2) of the plastically deformable wires (104), the proximal end portion of the first wire does not cross over or under the proximal end portion of the second wire. For example, in the first pair (104-1) of plastically deformable wires (104), the proximal end portion (104-1*a* pep) of the first pair, first wire (104-1*a*) does not cross over or under the proximal end portion (104-1*b* pep) of the first pair, second wire (104-1*b*). Additionally, for example, in the second pair (104-2) of plastically deformable wires (104), the proximal end portion (104-2*a* pep) of the second pair, first wire (104-2*a*) does not cross over or under the proximal end portion (104-2*b* pep) of the second pair, second wire (104-2*b*).

Alternatively, in exemplary embodiments, as shown in FIGS. 2A, 2B, 2C, and 3B, in the support (wire mesh) proximal portion (200*pp*), all of the paired plastically deformable wires (204) have proximal end portions (204-1*a* pep, 204-1*b* pep, 204-2*a* pep, 204-2*b* pep) that cross over or under each other, whereby, in each pair (204-1, 204-2) of the plastically deformable wires (204), the proximal end portion of the first wire crosses over or under the proximal end portion of the second wire. For example, in the first pair (204-1) of plastically deformable wires (204), the proximal end portion (204-1*a* pep) of the first pair, first wire (204-1*a*) crosses over or under the proximal end portion (204-1*b* pep) of the first pair, second wire (204-1*b*). Additionally, for example, in the second pair (204-2) of plastically deformable wires (204), the proximal end portion (204-2*a* pep) of the second pair, first wire (204-2*a*) crosses over or under the proximal end portion (204-2*b* pep) of the second pair, second wire (204-2*b*).

Support (Wire Mesh) Distal Portion, and the Plastically Deformable Wires Therein The herein disclosed asymmetric external support (100; 200) was developed in a 'customizable' manner, according to different particular scenarios, conditions, and parameters of different CABG procedures, and based on actual empirical (clinical) data and information obtained from performing CABG procedures using external supports on arterial vein grafts. Such customization was implemented in order to produce different possible embodiments/configurations of the support (wire mesh) distal portion (100*dp*; 200*dp*) wherein the paired plastically deformable wires (104; 204) are configured with pairs of inter-looped distal end portions (i.e., in each pair of the plastically deformable wires, a first wire has a distal end portion configured as a first loop, that is inter-looped with a second loop of a second wire distal end portion.

In different exemplary embodiments, the plastically deformable wires distal end portions (loops) exhibit different degrees of mobility (i.e., from relatively high mobility to relatively low mobility), or full immobility (i.e., being fixed). Since the support (wire mesh) distal portion (100*dp*; 200*dp*) consists of the non-paired elastic wires (102; 202) closely braided or meshed (intertwined, interwoven) with, and physically contacting, the paired plastically deformable wires (104; 204), therefore, particular structural/mechanical configurations, along with mobility, or immobility, of the paired plastically deformable wires inter-looped distal end portions (loops) can, and are expected to, affect the structural/mechanical performance of immediately adjacent, and neighboring, non-paired elastic wires (102; 202) in the support (wire mesh) distal portion (100*dp*; 200*dp*). Thus, particular structural/mechanical configurations, along with mobility, or immobility, of the paired plastically deformable wires inter-looped distal end portions (loops) are directly related to, and determine, structural/mechanical performance of the support (wire mesh) distal portion (100*dp*; 200*dp*), in particular, and of the overall support (wire mesh) (100; 200), in general.

Customization of different possible embodiments/configurations of the asymmetric external support (100; 200), in general, and of the support (wire mesh) distal portion (100*dp*; 200*dp*), in particular, can translate into having support 'structural/mechanical' features exhibit different (favorable) performance characteristics during initial application and implantation (via an operator) of the support, and during the lifetime (in a patient) of the support. That, in turn, can translate into further improving SVG patency and safe use, as well as operator (e.g., surgeon) handling and manipulating characteristics, of the support for externally stenting an arterial vein graft used in a human CABG procedure.

Inter-Looped Distal End Portions (Loops) of the Plastically Deformable Wires

With reference to FIGS. 1, 2, and 4, in the support (wire mesh) distal portion (100*dp*; 200*dp*), the paired plastically deformable wires (104; 204) are configured with inter-looped distal end portions (loops), whereby each pair (104-1, 104-2; 204-1, 204-2) of the plastically deformable wires (104; 204) has a first wire distal end portion formed as a first wire closed loop [1st loop] that is looped (i.e., inter-looped) with a second wire distal end portion formed as a second wire closed loop [2nd loop]. In such embodiments, each pair of the plastically deformable wires has a first wire whose distal end portion forms a first wire closed loop [1st loop] with a first wire loop end back-folded upon the first wire (so as to close the 1st loop), and has a second wire whose distal end portion forms a second wire closed loop [2nd loop] with a second wire loop end looped (inter-looped) through the first wire closed loop and back-folded upon the second wire (so as to close the 2nd loop).

For example, in the support (wire mesh) distal portion (100*dp*; 200*dp*), in the first pair (104-1; 204-1) of paired plastically deformable wires (104; 204), the first pair, first wire (104-1*a*; 204-1*a*) is configured with an inter-looped distal end portion (104-1*a* dep [1st pair, 1st loop]; 204-1*a* [1st pair, 1st loop]), and the first pair, second wire (104-1*b*; 204-1*b*) is configured with an inter-looped distal end portion (104-1*b* dep [1st pair, 2nd loop]; 204-1*b* dep [1st pair, 2nd loop]). The first pair, first wire distal end portion (104-1*a* dep; 204-1*a* dep) forms a first pair, first wire closed loop [1st pair, 1st loop], with the end (tip) of the first pair, first wire closed loop [1st pair, 1st loop] back-folded upon the first pair, first wire (104-1*a*; 204-1*a*) (so as to close the first pair, first wire closed loop [1st pair, 1st loop]). The first pair, second wire distal end portion (104-1*b* dep; 204-1*b* dep) forms a first pair, second wire closed loop [1st pair, 2nd loop], with the end (tip) of the first pair, second wire closed loop [1st pair, 2nd loop] looped (inter-looped) through the first pair, first wire closed loop [1st pair, 1st loop] and back-folded upon the first pair, second wire (104-1*b*; 204-1*b*) (so as to close the first pair, second wire closed loop [1st pair, 2nd loop]).

Additionally, for example, in the support (wire mesh) distal portion (100*dp*; 200*dp*), in the second pair (104-2; 204-2) of paired plastically deformable wires (104; 204), the second pair, first wire (104-2*a*; 204-2*a*) is configured with an inter-looped distal end portion (104-2*a* dep [2nd pair, 1st loop]; 204-2*a* dep [2nd pair, 1st loop]), and the second pair, second wire (104-2*b*; 204-2*b*) is configured with an inter-looped distal end portion (104-2*b* dep [2nd pair, 2nd loop]; 204-2*b* dep [2nd pair, 2nd loop]). The second pair, first wire distal end portion (104-2*a* dep; 204-2*a* dep) forms a second pair, first wire closed loop [2nd pair, 1st loop], with the end (tip) of the second pair, first wire closed loop [2nd pair, 1st loop] back-folded upon the second pair, first wire (104-2*a*; 204-2*a*) (so as to close the 2nd pair, first wire closed loop [2nd pair, 1st loop]). The second pair, second wire distal end portion (104-2*b* dep; 204-2*b* dep) forms a second pair, second wire closed loop [2nd pair, 2nd loop], with the end (tip) of the second pair, second wire loop end [2nd pair, 2nd loop] looped (inter-looped) through the second pair, first wire closed loop [2nd pair, 1st loop] and back-folded upon the second pair, second wire (104-2*b*; 204-2*b*) (so as to close the 2nd pair, second wire closed loop [2nd pair, 2nd loop]).

In such embodiments, the 'back-fold' of each wire loop end upon its respective wire can have different particular configurations. In exemplary embodiments, the 'back-fold' of the wire loop end upon the wire is configured, whereby the ultimate end or tip (i.e., the utmost, farthest, or most distant part) of the wire loop end is aligned (so as to be co-axial/co-linear), and makes physical contact, with a particular segment or point along the remaining part of its respective wire. Alternatively, in exemplary embodiments, the 'back-fold' of the wire loop end upon the wire is configured, whereby the ultimate end or tip (i.e., the utmost, farthest, or most distant part) of the wire loop end crosses over or under, and onto its respective wire, in an 'x-like' transverse manner, so as to slightly extend past the wire (e.g., by a relatively small distance of 0.2 mm-2 mm), with a particular segment of that extended wire making physical contact with a particular segment or point along the remaining part of its respective wire.

Mobility/Immobility of the Plastically Deformable Wires Inter-Looped Distal End Portions (Loops)

Regarding mobility of the inter-looped distal end portions (loops), with reference to FIGS. 1, 2, and 4, in exemplary embodiments, in the support (wire mesh) distal portion (100*dp*; 200*dp*), in each pair (104-1, 104-2; 204-1, 204-2) of the plastically deformable wires (104; 204), and in the inter-looped distal end portions, the two individual loops (i.e., the two individual looped distal end portions that are inter-looped with each other) are configured so as to be (longitudinally or/and radially) slidably movable relative to each other. In such embodiments, the loop (inter-looped distal end portion) of the first wire and the loop (inter-looped distal end portion) of the second wire, are (longitudinally or/and radially) slidably movable relative to each other. Equivalently stated, in each pair (104-1, 104-2; 204-1, 204-2) of the plastically deformable wires (104; 204), the first wire distal end portion (formed as the first wire closed loop [1st loop]) and the second wire distal end portion (formed as the second wire closed loop [2nd loop]), that are inter-looped with each other, are configured so as to be (longitudinally or/and radially) slidably movable relative to each other.

For example, in the first pair (104-1; 204-1) of plastically deformable wires (104; 204), the first pair, first wire looped distal end portion (104-1*a* dep [1st pair, 1st loop]; 204-1*a* [1st pair, 1st loop]) and the first pair, second wire looped distal end portion (104-1*b* dep [1st pair, 2nd loop]; 204-1*b* dep [1st pair, 2nd loop]), that are inter-looped with each other, are configured so as to be (longitudinally or/and radially) slidably movable relative to each other. Additionally, for example, in the second pair (104-2; 204-2) of plastically deformable wires (104; 204), the second pair, first wire looped distal end portion (104-2*a* dep [2nd pair, 1st loop]; 204-2*a* dep [2nd pair, 1st loop]) and the second pair, second wire looped distal end portion (104-2*b* dep [2nd pair, 2nd loop]; 204-2*b* dep [2nd pair, 2nd loop]), that are inter-looped with each other, are configured so as to be (longitudinally or/and radially) slidably movable relative to each other.

Such exemplary embodiments of the inter-looped distal end portions (loops) being slidably movable relative to each other require that, not both, but, at least one, of the two individual loops (i.e., at least one of the two individual looped distal end portions that are inter-looped with each other) in each pair (104-1, 104-2; 204-1, 204-2) of the plastically deformable wires (104; 204) is configured with a sufficiently large loop size that facilitates the (radial or/and longitudinal) slidable mobility of the two loops relative to each other. In exemplary embodiments, not one, but, both of the two individual loops in each pair (104-1, 104-2; 204-1, 204-2) of the plastically deformable wires (104; 204) are configured with a sufficiently large loop size that facilitates the slidable mobility of the two loops relative to each other.

Regarding immobility of the inter-looped distal end portions (loops), with reference to FIGS. 1, 2, and 4, in exemplary embodiments, in the support (wire mesh) distal portion (100*dp*; 200*dp*), in each pair (104-1, 104-2; 204-1, 204-2) of the plastically deformable wires (104; 204), and in the inter-looped distal end portions, the two individual loops (i.e., the two individual looped distal end portions that are inter-looped with each other) are configured so as not to be slidably movable (i.e., they are immobile, or fixed in place) relative to each other. In such embodiments, the loop (inter-looped distal end portion) of the first wire and the loop (inter-looped distal end portion) of the second wire, are not (longitudinally or/and radially) slidably movable relative to each other, rather, the loops of the first and second wires are immobile, or fixed, relative to each other. Equivalently stated, in each pair (104-1, 104-2; 204-1, 204-2) of the plastically deformable wires (104; 204), the first wire distal end portion (formed as the first wire closed loop [1st loop]) and the second wire distal end portion (formed as the second wire closed loop [2nd loop]), that are inter-looped with each other, are configured so as not to be slidably movable (i.e., they are immobile, or fixed in place) relative to each other.

For example, in the first pair (104-1; 204-1) of plastically deformable wires (104; 204), the first pair, first wire looped distal end portion (104-1*a* dep [1st pair, 1st loop]; 204-1*a* [1st pair, 1st loop]) and the first pair, second wire looped distal end portion (104-1*b* dep [1st pair, 2nd loop]; 204-1*b* dep [1st pair, 2nd loop]), that are inter-looped with each other, are configured so as not to be slidably movable (i.e., they are immobile, or fixed in place) relative to each other. Additionally, for example, in the second pair (104-2; 204-2) of plastically deformable wires (104; 204), the second pair, first wire looped distal end portion (104-2*a* dep [2nd pair, 1st loop]; 204-2*a* dep [2nd pair, 1st loop]) and the second pair, second wire looped distal end portion (104-2*b* dep [2nd pair, 2nd loop]; 204-2*b* dep [2nd pair, 2nd loop]), that are inter-looped with each other, are configured so as not to be slidably movable (i.e., they are immobile, or fixed in place) relative to each other.

Such exemplary embodiments of the inter-looped distal end portions (loops) not being slidably movable (i.e., being immobile, fixed in place) relative to each other require that, not both, but, at least one, of the two individual loops (i.e., at least one of the two individual looped distal end portions that are inter-looped with each other) in each pair (104-1, 104-2; 204-1, 204-2) of the plastically deformable wires (104; 204) is configured with a sufficiently small loop size that fully prevents (radial or longitudinal) slidable mobility of the two loops relative to each other. In exemplary embodiments, not one, but, both of the two individual loops in each pair (104-1, 104-2; 204-1, 204-2) of the plastically deformable wires (104; 204) are configured with a sufficiently small loop size that fully prevents slidable mobility of the two loops relative to each other.

For the above described exemplary embodiments/configurations of the support (wire mesh) distal portion (100*dp*; 200*dp*) that exhibit different degrees of mobility (i.e., from relatively high mobility to relatively low mobility), or full immobility (i.e., being fixed), in the paired plastically deformable wires inter-looped distal end portions (loops), the loop size may be quantifiable and measurable, for example, in terms of the inner [circular or elliptical loop-shape] area of, and encompassed by, a single loop, which is then used for (custom) designing, and subsequently forming, the inter-looped distal end portions (loops) of the paired plastically deformable wires (104; 204) in the support (wire mesh) distal portion (100*dp*; 200*dp*). Accordingly, for such exemplary embodiments, having the ability to control the loop size (i.e., inner [loop-shape] area of each loop), translates into having the ability to control the degree or extent of mobility, or immobility, provided to the paired plastically deformable wires inter-looped distal end portions (loops) in the support (wire mesh) distal portion (100*dp*; 200*dp*). This, in turn, facilitates the asymmetric external support (100; 200) structural/mechanical features to exhibit different (favorable) 'customized' performance characteristics during initial application and implantation (via an operator) of the support, and during the lifetime (in a patient) of the support.

Securing (Reinforcing) Closure of the Plastically Deformable Wires Inter-Looped Distal End Portions (Loops)

As illustratively described above, each pair of the plastically deformable wires has a first wire whose distal end portion forms a first wire closed loop [1st loop] with a first wire loop end back-folded upon the first wire (so as to close the 1st loop), and has a second wire whose distal end portion forms a second wire closed loop [2nd loop] with a second wire loop end looped (inter-looped) through the first wire closed loop and back-folded upon the second wire (so as to close the 2nd loop). The inventor observed that for each wire, despite each closed loop having its end back-folded upon the wire (so as to close the loop), the possibility exists that its closed loop may loosen, become unlooped, and open up, during initial application and implantation of the support by an operator of the CABG procedure, or/and during the lifetime of the support in a patient, which, could lead to the support (wire mesh) distal portion (100*dp*; 200*dp*), with wires of the open loop(s), injuring (via plastically deformable wires pricking or piercing) heart or/and vascular tissue.

To address, and prevent, this potential problem associated with the paired plastically deformable wires inter-looped distal end portions (loops) in the support (wire mesh) distal portion (100*dp*; 200*dp*), the inventor developed exemplary embodiments of the herein disclosed asymmetric external support (100; 200) that include securing (reinforcing) closure of the loops (loop closures). Such exemplary embodiments are based on using a loop closure securing (reinforcing) procedure, in particular, (i) a loop closure adhering procedure, or (ii) a loop closure heat treatment (e.g., a laser welding, or a laser soldering) procedure.

Accordingly, in such exemplary embodiments, with reference to FIGS. 1, 2, and 4, in the support (wire mesh) distal portion (100*dp*; 200*dp*), in each inter-looped pair (104-1, 104-2; 204-1, 204-2) of the plastically deformable wires (104; 204), each inter-looped distal end portion (loop) has a loop closure (i.e., the closure [closed part] of the loop) that is individually secured or reinforced, via use of a loop closure securing (reinforcing) procedure, in particular, above listed (i) or (ii). Moreover, each loop closure (the closure [closed part] of each loop of the two (inter-looped) loops in each inter-looped distal end portion) is individually secured or reinforced (via above (i) or (ii)), specifically at the particular location or point which the wire loop end is back-folded upon, and makes physical contact with, its respective wire.

Regarding (i) a loop closure adhering procedure, in exemplary embodiments, in the support (wire mesh) distal portion (100*dp*; 200*dp*), in each inter-looped pair (104-1, 104-2; 204-1, 204-2) of the plastically deformable wires (104; 204), each inter-looped distal end portion (loop) has a loop closure (i.e., the closure [closed part] of the loop) that may be individually secured or reinforced, via a loop closure adhering procedure, with adhesive material (e.g., medical grade glue or other adhesive type material) that is applied to the particular location or point at which the wire loop end is back-folded upon, and makes physical contact with, its respective wire.

For example, in the support (wire mesh) distal portion (100*dp*; 200*dp*), in the first pair (104-1; 204-1) of paired plastically deformable wires (104; 204), the first pair, first wire (104-1*a*; 204-1*a*) has an inter-looped distal end portion (104-1*a* dep [1st pair, 1st loop]; 204-1*a* [1st pair, 1st loop]) with a loop closure that may be individually secured or reinforced, via a loop closure adhesive procedure, with adhesive material that is applied to the particular location or point at which the wire loop end is back-folded upon, and makes physical contact with, the first pair, first wire (104-1*a*; 204-1*a*).

Regarding (ii) a loop closure heat treatment procedure, in exemplary embodiments, in the support (wire mesh) distal portion (100*dp*; 200*dp*), in each inter-looped pair (104-1, 104-2; 204-1, 204-2) of the plastically deformable wires (104; 204), each inter-looped distal end portion (loop) has a loop closure (i.e., the closure [closed part] of the loop) that may be individually secured or reinforced, via a loop closure heat treatment procedure, with welding or soldering applied to the particular location or point at which the wire loop end is back-folded upon, and makes physical contact with, its respective wire.

For example, in the support (wire mesh) distal portion (100*dp*; 200*dp*), in the first pair (104-1; 204-1) of paired plastically deformable wires (104; 204), the first pair, first wire (104-1*a*; 204-1*a*) has an inter-looped distal end portion (104-1*a* dep [1st pair, 1st loop]; 204-1*a* [1st pair, 1st loop]) with a loop closure that may be individually secured or reinforced, via a loop closure heat treatment procedure, with welding or soldering applied to the particular location or point at which the wire loop end is back-folded upon, and makes physical contact with, the first pair, first wire (104-1*a*; 204-1*a*).

For the exemplary embodiments of (i) and (ii), the loop closure securing (reinforcing) procedure can be performed in order to produce different possible embodiments/configurations of the individually secured (reinforced) loop closures, such that in each pair (104-1, 104-2; 204-1, 204-2) of the plastically deformable wires (104; 204), and in the inter-looped distal end portions thereof, the two closed loops with their two respective individually secured (reinforced) loop closures, can exhibit different degrees of relative mobility, or full immobility (i.e., being fixed), as described hereinabove.

For example, in the first pair (104-1; 204-1) of paired plastically deformable wires (104; 204), for the first pair, first wire (104-1a; 204-1a) and the first pair, second wire (104-1b; 204-1b), the two loop closures can be individually subjected to the loop closure securing (reinforcing) procedure (via above (i) or (ii)), in order to produce two respective individually secured (reinforced) loop closures, such that the first pair, first wire inter-looped distal end portion (104-1a dep [1st pair, 1st loop; 204-1a dep [1st pair, 1st loop]) and the first pair, second wire inter-looped distal end portion (104-1b dep [1st pair, 2nd loop]; 204-1b dep [1st pair, 2nd loop]) are to some degree (longitudinally or/and radially) slidably movable relative to each other.

Alternatively, for example, in the first pair (104-1; 204-1) of paired plastically deformable wires (104; 204), for the first pair, first wire (104-1a; 204-1a) and the first pair, second wire (104-1b; 204-1b), the two loop closures can be subjected to the loop closure securing (reinforcing) procedure (via above (i) or (ii)), in order to produce two respective individually secured (reinforced) loop closures, such that the first pair, first wire inter-looped distal end portion (104-1a dep [1st pair, 1st loop; 204-1a dep [1st pair, 1st loop]) and the first pair, second wire inter-looped distal end portion (104-1b dep [1st pair, 2nd loop]; 204-1b dep [1st pair, 2nd loop]) are not slidably movable (i.e., they are immobile, or fixed in place) relative to each other.

Implementation of the above described loop closure securing (reinforcing) procedure, to produce the indicated exemplary embodiments of the support (wire mesh) (100; 200), provides assurance that, during initial application and implantation of the support, and during the lifetime of the support in a patient, each closed loop with its individually secured (reinforced) loop closure (exhibiting either relative mobility, or full immobility), will not loosen, become unlooped, and open up.

Longitudinal Offset (λ) of the Inter-Looped Distal End Portions (Loops) of the Plastically Deformable Wires The herein disclosed asymmetric external support (100; 200) was designed, and constructed, wherein the support (wire mesh) distal portion (100dp; 200dp) is configured with the paired plastically deformable wires (104; 204) longitudinally extending along less than the full longitudinal length (L) of the support (wire mesh) (100; 200), whereby the apexes (i.e., the midpoints of the arched parts) of all the looped distal end portions (loops) are proximally longitudinally offset from, and not coincident with, the support (wire mesh) distal end (100de; 200de). In exemplary embodiments, the support (wire mesh) proximal portion (100pp; 200pp) is configured with all the paired plastically deformable wires (104; 204) having proximal ends that are coincident with the support (wire mesh) proximal end (100pe; 200pe). Alternatively, in exemplary embodiments, the support (wire mesh) proximal portion (100pp; 200pp) is configured with not all (e.g., only one of, or even none of) the paired plastically deformable wires (104; 204) having proximal ends that are coincident with the support (wire mesh) proximal end (100pe; 200pe).

As shown in FIGS. 1, 2, and 4, the paired plastically deformable wires (104; 204) longitudinally extend along less than the full longitudinal length (L) of the support (wire mesh) (100; 200), whereby the apexes (midpoints of the arched parts) of all the looped distal end portions (104-1a dep [1st pair, 1st loop], 104-1b [1st pair, 2nd loop], 104-2a dep [2nd pair, 1st loop], 104-2b dep [2nd pair, 2nd loop]; 204-1a dep [1st pair, 1st loop], 204-1b [1st pair, 2nd loop], 204-2a dep [2nd pair, 1st loop], 204-2b dep [2nd pair, 2nd loop]) are proximally longitudinally offset from, and not coincident with, the support (wire mesh) distal end (100de; 200de). In such embodiments, the proximal ends (104-1a pe, 104-1b pe, 104-2a pe, 104-2b pe; 204-1a pe, 204-1b pe, 204-2a pe, 204-2b pe) of all the paired plastically deformable wires (104; 204) are coincident with the support (wire mesh) proximal end (100pe; 200pe).

The 'longitudinal offset' is indicated as, and referred to by, the reference symbol X (lambda). In exemplary embodiments, the proximal longitudinal offset (X), of the apex (midpoint of the arched part) of each looped (inter-looped) distal end portion (loop) of each plastically deformable wire (104; 204) from the (ultimate) distal end (100de; 200de) of the support (wire mesh) (100; 200), has a magnitude in a range of between 0.2 mm and 1.5 mm.

As a first specific example, as particularly shown in the figures, for the first pair, first wire (104-1a; 204-1a) of plastically deformable wires (104; 204), the apex (arched part midpoint) of the looped distal end portion (104-1a dep [1st pair, 1st loop]; 204-1a dep [1st pair, 1st loop]) has a proximal longitudinal offset (k) from the support (wire mesh) distal end (100de; 200de), and the proximal end (104-1a pe; 204-1a pe) of the first pair, first wire (104-1a; 204-1a) is coincident with the support (wire mesh) proximal end (100pe; 200pe).

As a second specific example, as particularly shown in the figures, for the second pair, second wire (104-2b; 204-2b) of plastically deformable wires (104; 204), the apex (arched part midpoint) of the looped distal end portion (104-2b dep [2nd pair, 2nd loop]; 204-2b dep [2nd pair, 2nd loop]) has a proximal longitudinal offset (k) from the support (wire mesh) distal end (100de; 200de), and the proximal end (104-2b pe; 204-2b pe) of the second pair, second wire (104-2b; 204-2b) is coincident with the support (wire mesh) proximal end (100pe; 200pe).

Radial Offset (Δ) of the Inter-Looped Distal End Portions (Loops) of the Plastically Deformable Wires Reference is made to FIGS. 1A, 2A, and 4A which particularly show the radial offset (A) of the inter-looped distal end portions (loops) of the plastically deformable wires (104; 204), compared to the other figures of the asymmetric external support (100; 200) wherein the radial offset (A) of the paired plastically deformable wires inter-looped distal end portions (loops) is present, but, not readily viewable.

The herein disclosed asymmetric external support (100; 200) was designed, and constructed, wherein the support (wire mesh) distal portion (100dp; 200dp) has all the paired plastically deformable wires (104; 204) configured such that the first and second wire closed loops of the inter-looped distal end portions radially extend beyond the outer radius ($R_o$) of the support (wire mesh) (100; 200). In such configurations, the apexes (midpoints of the arched parts) of all the looped (inter-looped) distal end portions (loops) are outwardly radially offset from, and not coincident with, the outer circumferential periphery (100*ocp*; 200*ocp*) of the support (wire mesh) (100; 200).

As described hereinabove, the non-paired elastic wires (102; 202) circumferentially outwardly facing external surfaces (spanning along, and parallel to, the full longitudinal length (L) of the support (wire mesh) (100; 200)) coincide with, and define, the support (wire mesh) outer circumferential periphery (100*ocp*; 200*ocp*). In the support (wire mesh) distal portion (100*dp*; 200*dp*), such radial extension beyond the outer radius ($R_o$) of the support (wire mesh) (100; 200), and outwardly radial offset from, and non-coincidence with, the support (wire mesh) outer circumferential periphery (100*ocp*; 200*ocp*), corresponds to the plastically deformable wires inter-looped distal end portions (loops) projecting (protruding, jutting, extending, sticking) out or outwardly from the outer radius ($R_o$) of the support (wire mesh) (100; 200), whereby the apexes (midpoints of the arched parts) of all the looped distal end portions (loops) project (protrude, jut, extend, stick) out or outwardly from the outer circumferential periphery (100*ocp*; 200*ocp*) of the support (wire mesh) (100; 200).

The 'radial offset' is indicated as, and referred to by, the reference symbol A (delta). In exemplary embodiments, the outward radial offset (A) of the apex (midpoint of the arched part) of each looped distal end portion of each plastically deformable wire (104; 204) out or outwardly from the outer circumferential periphery (100*ocp*; 200*ocp*) of the support (wire mesh) (100; 200), has a magnitude in a range of between 0.2 mm and 1.5 mm.

As a first specific example, as particularly shown in FIGS. 1A, 2A, and 4A, for the second pair, first wire (104-2*a*; 204-2*a*) of plastically deformable wires (104; 204), the looped distal end portion (104-2*a* dep [2nd pair, 1st loop]; 204-2*a* dep [2nd pair, 1st loop]) radially extends beyond the outer radius ($R_o$) of the support (wire mesh) (100; 200), whereby the apex (arched part midpoint) of that looped distal end portion has an outward radial offset (A) from, and is not coincident with, the outer circumferential periphery (100*ocp*; 200*ocp*) of the support (wire mesh) (100; 200).

As a second specific example, also shown in FIGS. 1A, 2A, and 4A, for the first pair, first wire (104-1*a*; 204-1*a*) of plastically deformable wires (104; 204), the looped distal end portion (104-1*a* dep [1st pair, 1st loop]; 204-1*a* dep [1st pair, 1st loop]) radially extends beyond the outer radius ($R_o$) of the support (wire mesh) (100; 200), whereby the apex (arched part midpoint) of that looped distal end portion has an outward radial offset (A) from, and is not coincident with, the outer circumferential periphery (100*ocp*; 200*ocp*) of the support (wire mesh) (100; 200).

Support (Wire Mesh) Middle Portion

In contrast to the above described longitudinal and radial asymmetric aspects of the asymmetric external support (wire mesh) opposing proximal and distal portions (100*pp*; 200*pp*), and of the paired plastically deformable wires (104; 204) therein, within the support (wire mesh) middle portion (100*mp*; 200*mp*), the structural (geometrical and mechanical) features, properties, and characteristics of the non-paired elastic wires (102; 202) are spatially, longitudinally and radially symmetric and uniform, and, the structural (geometrical and mechanical) features, properties, and characteristics of the paired plastically deformable wires (104; 204) are spatially, longitudinally and radially symmetric and uniform.

Asymmetric Features of the Asymmetric External Support

Based on the above illustratively described numerous structural (geometrical and mechanical) aspects of the herein disclosed asymmetric external support, the asymmetric external support (100; 200) is spatially, 'longitudinally and radially' asymmetric (i.e., lacks symmetry) with respect to the opposing proximal and distal portions (100*pp*; 200*pp*, and 100*dp*; 200*dp*), and the respective opposing proximal and distal ends therein (100*pe*; 200*pe*, and 100*de*; 200*de*). Specifically, in the herein disclosed asymmetric external support (100; 200), particular structural (geometrical and mechanical) features, properties, and characteristics are spatially, 'longitudinally and radially asymmetric' with respect to the opposing proximal and distal portions (100*pp*; 200*pp*, and 100*dp*; 200*dp*), and the respective opposing proximal and distal ends (100*pe*; 200*pe*, and 100*de*; 200*de*) therein. More specifically, the support (wire mesh) distal portion (100*dp*; 200*dp*), including the distal end (100*de*; 200*de*) therein, exhibits, and is characterized by, particular structural (geometrical and mechanical) features, properties, and characteristics that are asymmetric relative to, and substantially different from, the particular structural (geometrical and mechanical) features, properties, and characteristics exhibited by, and characterizing, the support (wire mesh) proximal portion (100*pp*; 200*pp*), including the proximal end (100*pe*; 200*pe*) therein.

A first asymmetric feature is that in the support (wire mesh) distal portion (100*dp*; 200*dp*), all paired plastically deformable wires (104; 204) are configured with looped distal end portions (104-1*a* dep [1st loop], 104-1*b* dep [2nd loop], 104-2*a* [1st loop], 104-2*b* [2nd loop]; 204-1*a* [1st loop], 204-1*b* [2nd loop], 204-2*a* [1st loop], 204-2*b* [2nd loop]) having closed ends, and in the support (wire mesh) proximal portion (100*pp*; 200*pp*), all paired plastically deformable wires are configured with non-looped, non-connected proximal end portions (104-1*a* pep, 104-1*b* pep, 104-2*a* pep, 104-2*b* pep; 204-1*a* pep, 204-1*b* pep, 204-2*a* pep, 204-2*b* pep) having open ends. Thus, while the support (wire mesh) distal portion (100*dp*; 200*dp*) is configured with looped pairs of plastically deformable wires having closed ends, the support (wire mesh) proximal portion (100*pp*; 200*pp*) is configured with non-looped, non-connected pairs of plastically deformable wires having open ends.

A second asymmetric feature is that the paired plastically deformable wires (104; 204) longitudinally extend along less than the full longitudinal length (L) of the support (wire mesh) (100; 200), whereby the apexes (midpoints of the arched parts) of all the looped distal end portions are proximally longitudinally offset from, and not coincident with, the (ultimate) distal end (100*de*; 200*de*) of the support (wire mesh) (100; 200). In exemplary embodiments, the proximal ends of all the paired plastically deformable wires are coincident with the (ultimate) proximal end (100*pe*; 200*pe*) of the support (wire mesh) (100; 200). Thus, in such exemplary embodiments, while the support (wire mesh) distal end (100*de*; 200*de*) is not coincident with the longitudinally offset apexes of all the looped distal end portions of the paired plastically deformable wires (104; 204), the support (wire mesh) proximal end (100*pe*; 200*pe*) is coincident with the proximal ends of all the paired plastically deformable wires (104; 204).

A third asymmetric feature is that in the support (wire mesh) distal portion (100*dp*; 200*dp*), all the paired plastically deformable wires (104; 204) are configured with the looped distal end portions (loops) radially extending beyond the outer radius ($R_o$) of the support (wire mesh) (100; 200), whereby the apexes (midpoints of the arched parts) of all the looped distal end portions (loops) are outwardly radially offset from, and not coincident with, the outer circumferential periphery (100*ocp*; 200*ocp*) of the support (wire mesh) (100; 200). Thus, while the outer circumferential periphery (100*ocp*; 200*ocp*) of the support (wire mesh) distal portion (100*dp*; 200*dp*) is not coincident with the radially offset apexes of all the looped distal end portions of the paired plastically deformable wires (104; 204), the outer circumferential periphery (100*ocp*; 200*ocp*) of the support (wire mesh) proximal portion (100*pp*; 200*pp*) is coincident with the proximal ends of all the paired plastically deformable wires (104; 204).

With respect to application of the herein disclosed asymmetric external support (100; 200) in a coronary arterial bypass graft (CABG) procedure, the asymmetric external support (100; 200) is externally applicable upon, to cover, a vein graft in a manner such that the support (wire mesh) distal portion (100*dp*; 200*dp*), with the support (wire mesh) distal end (100*de*; 200*de*) therein, is positionable at a coronary artery anastomosis site, and the support (wire mesh) proximal portion (100*pp*; 200*pp*), with the support (wire mesh) proximal end (100*pe*; 200*pe*) therein, is positionable at an other anastomosis site.

Positioning of the support (wire mesh) distal portion (100*dp*; 200*dp*), with the support (wire mesh) distal end (100*de*; 200*de*) therein, at the coronary artery anastomosis site, facilitates exploitation of the above described asymmetric features of the asymmetric external support. Namely, according to such particular directional positioning, following the vein graft distal end being anastomized directly to the coronary artery, the apexes of all the looped distal end portions (loops), and therefore, the distal-most parts, of all the paired plastically deformable wires (104; 204) in the support (wire mesh) distal portion (100*dp*; 200*dp*) will be proximally longitudinally located away (by more than the loops apexes proximal longitudinal offset (k) [e.g., 0.2 mm-1.5 mm]) from, and not coincident with, the coronary artery anastomosis site. This results in eliminating, or at least minimizing, possibility that the apexes (distal-most parts) of the paired plastically deformable wires looped distal end portions (loops) will injure (via pricking or piercing) heart or/and vascular tissue in the immediate vicinity of the coronary artery anastomosis site.

Positioning of the support (wire mesh) proximal portion (100*pp*; 200*pp*), with the support (wire mesh) proximal end (100*pe*; 200*pe*) therein, at an other anastomosis site, facilitates subsequent anastomosis of the support (wire mesh) proximal end (100*pe*; 200*pe*) to that other anastomosis site. In a coronary arterial bypass graft (CABG) procedure, exemplary other anastomosis sites are: (1) the aorta (more than 90% of time); (2) another venous graft (e.g., an SVG) anastomized directly to the aorta; (3) an arterial graft (e.g., a radial artery graft) anastomosed to a coronary artery and to the aorta; and (4) an internal mammary artery.

Exemplary Materials of Construction, and Exemplary Size Dimensions, of Components and Structural Features of the Asymmetric External Support The following, in a non-limiting manner, is presentation of exemplary materials of construction, and exemplary size dimensions, of components and structural features of the herein disclosed asymmetric external support. Implementation and practice of embodiments of the herein disclosed invention are not limited to the below presented exemplary materials and size dimensions. Alternative or additional materials of construction and size dimensions may be used for implementing and practicing embodiments of the herein disclosed invention.

Overall Support (Tubular Wire Braid or Mesh) 100; 200

Length (L): 2.5 cm-12 cm; for example, 6, 7, or 8 cm, in its longitudinally 'relaxed' configuration, prior to deployment and in-vivo implantation via a CABG procedure. 7 cm-36 cm, in its longitudinally 'expanded' configuration after deployment and in-vivo implantation via a CABG procedure.

Outer radius ($R_o$): 1.75 mm-7.5 mm; outer diameter: 3.5 mm-15 mm.

Wire mesh braiding angle: 0 degrees-180 degrees; for example, 10 degrees, 30 degrees, 45 degrees, 60 degrees, 90 degrees, 120 degrees, 150 degrees.

Total number of wires (fibers, filaments, threads): 24-156. For example, 24, 36, 42, 64, 128, 156 individual (non-paired elastic+plastically deformable) wires.

Non-Paired Elastic Wires (Fibers, Filaments, Threads) 102: 202

Materials: cold worked metals, or cold worked metal alloys, for example, of cobalt, chrome, nickel, titanium, aluminum, stainless steel; characterized by exhibiting 'elasticity', being 'elastic', and having 'elastic' properties.

Diameter: 10 Microns (0.01 cm)-100 Microns (0.1 cm).

Total number of individual elastic wires in tubular wire mesh (100; 200): 20-124. For example, 20, 38, 60, 124 individual, non-paired elastic wires.

Paired Plastically Deformable Wires (Fibers, Filaments, Threads) 104; 204

Materials: heat treated (hot worked, annealed) metals, or heat treated (hot worked, annealed) metal alloys, for example, of cobalt, chrome, nickel, titanium, aluminum, stainless steel; characterized by exhibiting 'plasticity', being 'plastically deformable', and having 'plastically deformable' properties.

Diameter: 50 microns (0.05 cm)-200 microns (0.2 cm).

Total number of individual plastically deformable wires in tubular wire mesh (100; 200): 4-32. For example, 2, 4, 8, 16, 32 individual, paired plastically deformable wires.

Plastically Deformable Wires Looped/Inter-Looped Distal End Portions (Loops) [1st Loop, 2nd Loop]

Single loop size (circular diameter, or non-circular (ellipse) long diameter): 0.2 mm-1.5 mm.

Proximal longitudinal offset (k): 0.2 mm-1.5 mm.

Outward radial offset (A): 0.2 mm-1.5 mm.

In exemplary embodiments, the loops of the support (wire mesh) are manually made (formed) by inserting a mandrel (rod, shaft) into the support (wire mesh) so as to firmly hold and fix the support (wire mesh) in place. The support (wire mesh), with mandrel inside, is then placed on the platform of a microscope, and a tweezer (pincers) is used to delicately manipulate and bend (fold, and back-fold) each plastically deformable wire distal end portion into the form of a (circular or elliptical shaped loop), followed by inter-looping two looped wires for forming an inter-looped pair of the plastically deformable wires. During that process, care is taken so as to prevent, or at least minimize, contacting the non-paired elastic wires, so as not to undesirably alter the braided (intertwined, interwoven) structure of the support (wire mesh). For each pair of the plastically deformable wires, the first wire distal end portion is formed into a first wire closed loop [1st loop] with a first wire loop end back-folded upon the first wire (so as to close the 1st loop). Then, for the same pair of plastically deformable wires, the second wire distal end portion is formed into a second wire closed loop [2nd loop], with a second wire loop end looped (inter-looped) through the first wire closed loop and back-folded upon the second wire (so as to close the 2nd loop).

Exemplary (Actual) Prototype of the Asymmetric External Support

Figure 6:
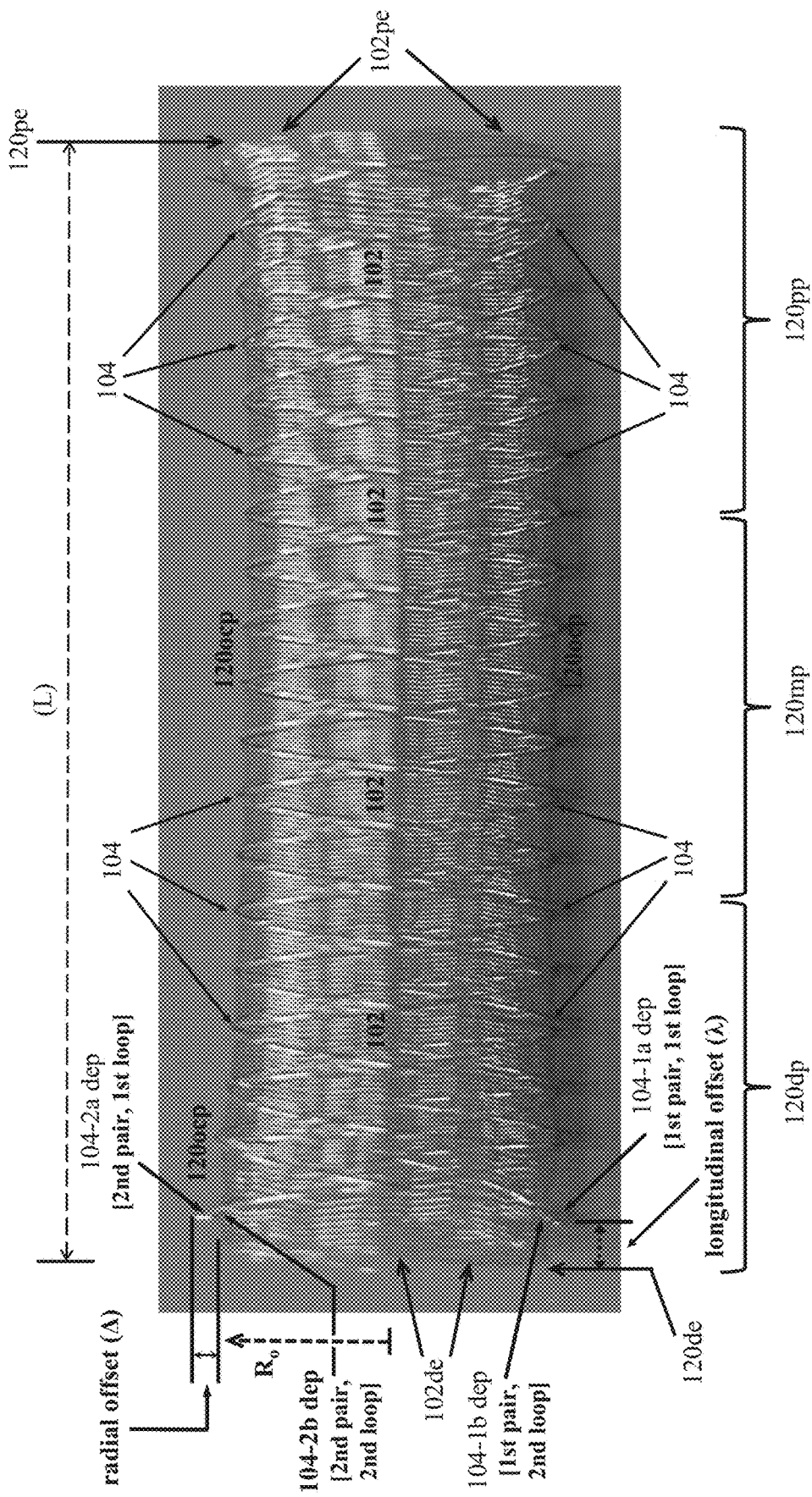
FIGS. 6 and 7 are exemplary micrographs of an exemplary (actual) prototype of the asymmetric external support, based on, and constructed in accordance with, the schematic embodiments of the exemplary asymmetric external support shown in FIGS. 1, 4, and 5, in accordance with some embodiments of the invention.
Figure 7:
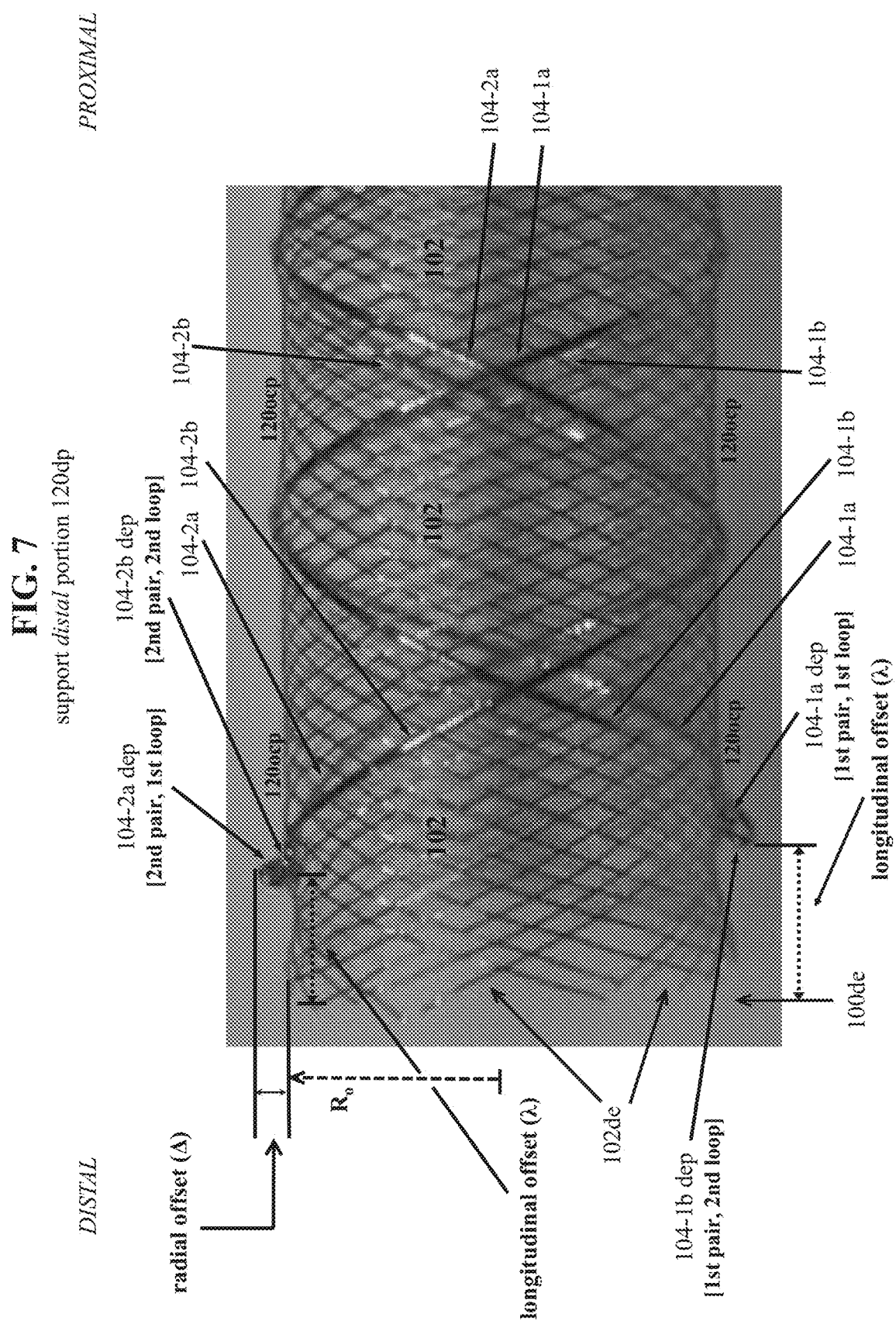

FIGS. 6 and 7 are exemplary micrographs (photographs as viewed through a microscope) of an exemplary (actual) prototype of the herein disclosed asymmetric external support [indicated as, and referred to by, reference number 120], for stabilizing a vein graft used in a coronary arterial bypass graft (CABG) procedure. Exemplary prototype asymmetric external support 120, shown in FIGS. 6 and 7, was designed and constructed in accordance with the schematic views of the exemplary embodiment of the asymmetric external support 100 shown in FIGS. 1A, 1B, 1C, 4A, 4B, 4C, and 5. In FIG. 6, the exemplary micrograph is of a top view of the exemplary prototype asymmetric external support 120, being analogous to the schematic top view of the exemplary asymmetric external support 100 shown in FIG. 1A. In FIG. 7, the exemplary micrograph is of a close-up top view of the distal portion of the exemplary prototype asymmetric external support 120, being analogous to the schematic close-up top view of the distal portion of the exemplary asymmetric external support 100 shown in FIG. 4A. Exemplary prototype asymmetric external support 120 shown in FIGS. 6 and 7 has all the same structural and functional features, characteristics, and properties as illustratively described above for exemplary asymmetric external support (wire mesh) 100 shown in FIGS. 1, 4, and 5. The same reference numbers, notation, and meanings thereof, used for illustratively describing exemplary asymmetric external support 100 shown in FIGS. 1, 4, and 5, equivalently apply for illustratively describing exemplary prototype asymmetric external support 120 shown in FIGS. 6 and 7.

Exemplary prototype asymmetric external support 120 is in the form of a tubular wire mesh longitudinally extending proximally and distally along the full longitudinal length (L) of the support [6.5 cm, in its relaxed configuration prior to deployment in a CABG procedure]. The prototype support (wire mesh) 120 has a proximal portion 120pp, a middle portion 120mp, a distal portion 120dp, a proximal end 120pe, a distal end 120de, and an outer circumferential periphery (boundary) 120ocp [with outer radius ($R_o$) equal to 3.5 mm (diameter of 7 mm)] that spans along, and parallel to, the full longitudinal length (L) of the prototype support (wire mesh) 120.

Prototype support (wire mesh) 120 is configured with non-paired elastic wires 102 [cobalt chrome, 0.038 mm (38 microns) diameter] and paired plastically deformable wires 104 [cobalt chrome, 0.106 mm (106 microns) diameter]. Prototype support (wire mesh) 120 has an exemplary total number of 42 wires (filaments), including an exemplary total number of 38 non-paired elastic wires (filaments) 102, and an exemplary total number of 4 paired plastically deformable wires (filaments) 104 corresponding to two pairs of two plastically deformable wires (filaments).

In the prototype support (wire mesh) proximal portion 120pp, the proximal ends of all the paired plastically deformable wires 104 are non-connected (i.e., not connected to any other wire of the prototype support (wire mesh)) and are open. Additionally, in the prototype support (wire mesh) proximal portion 120pp, all of the paired plastically deformable wires 104 have proximal end portions that do not cross over or under each other, whereby, in each pair (104-1, 104-2) of the plastically deformable wires (104), the proximal end portion of the first wire does not cross over or under the proximal end portion of the second wire.

In the prototype support (wire mesh) middle portion 120mp, the structural (geometrical and mechanical) features, properties, and characteristics of the non-paired elastic wires 102 and of the paired plastically deformable wires 104, are spatially, longitudinally and radially symmetric and uniform.

In the prototype support (wire mesh) distal portion 120dp, the paired plastically deformable wires 104 are configured with (longitudinally and radially offset) inter-looped distal end portions (loops). Each pair 104-1, 104-2 of the plastically deformable wires 104 has a first wire distal end portion formed as a first wire closed loop [1st loop] that is looped (i.e., inter-looped) with a second wire distal end portion formed as a second wire closed loop [2nd loop]. In each inter-looped pair 104-1, 104-2 of the plastically deformable wires 104, each inter-looped distal end portion (loop) is configured with a loop closure (i.e., the closure [closed part] of the loop) that is individually secured or reinforced, via a loop closure heat treatment procedure, by welding the particular location or point at which the wire loop end is back-folded upon, and makes physical contact with, its respective wire. In the inter-looped distal end portions, the two individual loops (i.e., the two individual looped distal end portions that are inter-looped with each other) are configured so as not to be slidably movable (i.e., they are immobile, or fixed in place) relative to each other.

In the prototype support (wire mesh) distal portion 120dp, the paired plastically deformable wires 104 longitudinally extend along less than the full longitudinal length (L) of the prototype support (wire mesh) 120, whereby the apexes (midpoints of the arched parts) of all the looped distal end portions (loops) are proximally longitudinally offset from, and not coincident with, the prototype support (wire mesh) distal end 120de. For each plastically deformable wire 104, the proximally longitudinal offset (k) of the apex (midpoint of the arched part) of each looped distal end portion (loop) from the (ultimate) distal end 120de of the prototype support (wire mesh) 120 has a magnitude of 0.75 mm.

In the prototype support (wire mesh) distal portion 120dp, the paired plastically deformable wires 104 are configured with the inter-looped distal end portions (loops) radially extending beyond the outer radius ($R_o$) of the prototype support (wire mesh) 120, whereby the apexes (midpoints of the arched parts) of all the looped distal end portions (loops) are outwardly radially offset from, and not coincident with, the outer circumferential periphery 120ocp of the prototype support (wire mesh) 120. For each plastically deformable wire 104, the outward radial offset (A) of the apex (midpoint of the arched part) of each looped distal end portion (loop) radially extending beyond the outer circumferential periphery 120ocp of the prototype support (wire mesh) 120 has a magnitude of 0.5 mm.

With respect to application of the exemplary prototype asymmetric external support 120, in a coronary arterial bypass graft (CABG) procedure, the prototype support 120 is externally applicable upon, to cover, a vein graft in a manner such that the prototype support (wire mesh) distal portion 120dp (with distal end 120de therein) is positionable at a coronary artery anastomosis site, and the prototype support (wire mesh) proximal portion 120pp (with proximal end 120pe therein) is positionable at an other anastomosis site.

Exemplary Applications of the Asymmetric External Support

Hereinabove illustratively described exemplary embodiments of the asymmetric external support (100 or 200) are particularly applicable in performing methods for externally supporting and stabilizing vein grafts used in coronary arterial bypass graft (CABG) procedures.

FIG. 8 is a schematic diagram showing an exemplary embodiment of application of the exemplary asymmetric external support 200 (e.g., shown in FIGS. 2A, 2B, 2C), in a CABG procedure, highlighting particular directional positioning of a vein graft (VG) externally covered and supported by exemplary asymmetric external support 200, with respect to a coronary artery anastomosis site (ca-AS) and another anastomosis site (o-AS).

As shown in FIG. 8, in the support proximal portion (200*pp*), the paired plastically deformable wires (204) have proximal end portions (e.g., 204-1*a* pep, and 204-1*b* pep) that cross over or under each other. In the support distal portion (200*dp*), the paired plastically deformable wires (204) are configured with inter-looped distal end portions (loops) (e.g., 204-1*a* dep [1st pair, 1st loop], and 204-1*b* dep [1st pair, 2nd loop]). The paired plastically deformable wires (204) longitudinally extend along less than the full longitudinal length (L) of the support 200, whereby the apexes of the looped distal end portions (204-1*a* dep [1st pair, 1st loop], 204-1*b* dep [1st pair, 2nd loop]) are proximally longitudinally offset from, and not coincident with, the support distal end (200*de*). The proximal ends (204-1*a* pe, 204-1*b* pe) of the paired plastically deformable wires (204) are coincident with the support proximal end (200*pe*).

In the CABG procedure, the asymmetric external support 200 is externally applicable upon, to cover, the vein graft (VG) in a manner such that the support distal portion (200*dp*), with the support distal end (200*de*) therein, will be positioned at the coronary artery anastomosis site (ca-AS), and the support proximal portion (200*pp*), with the support proximal end (200*pe*) therein, will be positioned at the other anastomosis site (o-AS).

Positioning of the support distal portion (200*dp*), with the support distal end (200*de*) therein, at the coronary artery anastomosis site (ca-AS), facilitates exploitation of the above illustratively described asymmetric features of the asymmetric external support 200. Namely, according to such particular directional positioning, after the distal end of the vein graft (VG) is anastomosed directly to the coronary artery (CA) at the coronary artery anastomosis site (ca-AS), the apexes of the looped distal end portions (loops) (204-1*a* dep [1st pair, 1st loop], and 204-1*b* [1st pair, 2nd loop]), and therefore, the distal-most parts, of the paired plastically deformable wires (204) in the support distal portion (200*dp*) will be proximally longitudinally located away (by more than the loops apexes proximal longitudinal offset (k) [e.g., 0.2 mm-1.5 mm]) from, and not coincident with, the coronary artery anastomosis site (ca-AS). This results in eliminating, or at least minimizing, possibility that the apexes (distal-most parts) of the paired plastically deformable wires looped distal end portions (loops) (204-1*a* dep [1st pair, 1st loop], and 204-1*b* dep [1st pair, 2nd loop]) will injure (via pricking or piercing) heart or/and vascular tissue in the immediate vicinity of the coronary artery anastomosis site (ca-AS).

Positioning of the support proximal portion (200*pp*), with the support proximal end (200*pe*) therein, at the other anastomosis site (o-AS), facilitates subsequent anastomosis of the support proximal end (200*pe*) to that other anastomosis site (o-AS). In a coronary arterial bypass graft (CABG) procedure, the other anastomosis site (o-AS) may be, for example: (1) the aorta (more than 90% of time); (2) another venous graft (e.g., an SVG) anastomized directly to the aorta; (3) an arterial graft (e.g., a radial artery graft) anastomized to a coronary artery and to the aorta; or (4) an internal mammary artery.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of', and 'consists of', as used herein, means 'including and limited to'.

Each of the phrases 'consisting essentially of', and 'consists essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to a single step, procedure, manner, means, or/and technique, or a sequence, set, or group of two or more steps, procedures, manners, means, or/and techniques, for accomplishing or achieving a given task or action. Any such herein disclosed method, in a non-limiting manner, may include one or more steps, procedures, manners, means, or/and techniques, that are known or readily developed from one or more steps, procedures, manners, means, or/and techniques, previously taught about by practitioners in the relevant field(s) and art(s) of the herein disclosed invention. In any such herein disclosed method, in a non-limiting manner, the stated or presented sequential order of one or more steps, procedures, manners, means, or/and techniques, is not limited to that specifically stated or presented sequential order, for accomplishing or achieving a given task or action, unless otherwise specifically defined or stated herein, or, unless the context clearly dictates otherwise. Accordingly, in any such herein disclosed method, in a non-limiting manner, there may exist one or more alternative sequential orders of the same steps, procedures, manners, means, or/and techniques, for accomplishing or achieving a same given task or action, while maintaining same or similar meaning and scope of the herein disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

The term 'about', as used herein, refers to ±10% of the stated numerical value.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

The invention claimed is:

1. An asymmetric external support for stabilizing a vein graft used in a coronary arterial bypass graft procedure, the asymmetric external support comprising:
   a tubular wire mesh longitudinally extending proximally and distally with wire mesh proximal, middle, and distal portions, and, wire mesh proximal and distal ends, said wire mesh is configured with non-paired elastic wires and paired plastically deformable wires;
   said non-paired elastic wires longitudinally extend along full longitudinal length of said wire mesh, whereby proximal and distal ends of said elastic wires coincide with said wire mesh proximal and distal ends, respectively;
   said wire mesh proximal portion has said proximal ends of all said paired plastically deformable wires being non-connected and open;
   said wire mesh distal portion has said paired plastically deformable wires configured with inter-looped distal end portions, whereby each pair of said plastically deformable wires has a first wire with a first wire distal end portion formed as a first wire closed loop that is inter-looped with a second wire distal end portion formed as a second wire closed loop of a second wire;
   said paired plastically deformable wires longitudinally extend along less than said full longitudinal length of said wire mesh, whereby apexes of all said inter-looped distal end portions are proximally longitudinally offset from, and not coincident with, said wire mesh distal end; and
   wherein, in the coronary arterial bypass graft procedure, the asymmetric external support is externally applicable upon, to cover, the vein graft in a manner such that said wire mesh distal end is positionable at a coronary artery anastomosis site, and said wire mesh proximal end is positionable at an other anastomosis site.

2. The external support of claim 1, wherein said wire mesh proximal portion is configured with all of said plastically deformable wires having proximal end portions not crossing over or under each other, whereby, in each pair of said plastically deformable wires, a first wire proximal end portion does not cross over or under a second wire proximal end portion.

3. The external support of claim 1, wherein said wire mesh proximal portion is configured with all of said plastically deformable wires having proximal end portions crossing over or under each other, whereby, in each pair of said plastically deformable wires, a first wire proximal end portion crosses over or under a second wire proximal end portion.

4. The external support of claim 1, wherein said wire mesh proximal portion is configured with all of said plastically deformable wires having said proximal ends coincident with said wire mesh proximal end.

5. The external support of claim 1, wherein, in each of said inter-looped distal end portions, said first wire distal end portion has a first wire loop end back-folded upon said first wire, and said second wire distal end portion has a second wire loop end looped through said first wire closed loop and back-folded upon said second wire.

6. The external support of claim 5, wherein back-fold of each of said first and second wire loop ends upon said first and second wires, respectively, is configured, whereby ultimate end or tip of each of said first and second wire loop ends is aligned, so as to be co-axial, and makes physical contact, with a segment or point along remaining part of said first or second wire, respectively.

7. The external support of claim 5, wherein back-fold of each of said first and second wire loop ends upon said first and second wires, respectively, is configured, whereby ultimate end or tip of each of said first and second wire loop ends crosses over or under, and onto said first or second wire, respectively, in an x-like transverse manner, so as to extend past said first or second wire, respectively, with a particular segment of said extended first or second wire, respectively, making physical contact with a particular segment or point along remaining part of said first or second wire, respectively.

8. The external support of claim 1, wherein, in said each pair of plastically deformable wires, said first wire distal end portion with said first wire closed loop and said second wire distal end portion with said second wire closed loop are configured so as to be longitudinally or/and radially slidably movable relative to each other.

9. The external support of claim 1, wherein, in said each pair of plastically deformable wires, said first wire distal end portion with said first wire closed loop and said second wire distal end portion with said second wire closed loop are configured so as not to be slidably movable relative to each other, and are immobile or fixed in place relative to each other.

10. The external support of claim 1, wherein, in said each pair of plastically deformable wires, each of said first wire closed loop and said second wire closed loop has a loop closure that is individually secured or reinforced, via use of a loop closure securing or reinforcing procedure.

11. The external support of claim 10, wherein said loop closure securing or reinforcing procedure is a loop closure adhering procedure, whereby adhesive material is applied to the location or point at which each of said first and second wire loop ends is back-folded upon, and makes physical contact with, said first and second wires, respectively.

12. The external support of claim 10, wherein said loop closure securing or reinforcing procedure is a loop closure heat treatment procedure, whereby welding or soldering is applied to the location or point at which each of said first and second wire loop ends is back-folded upon, and makes physical contact with, said first and second wires, respectively.

13. The external support of claim 1, wherein said proximal longitudinal offset of each one of said apexes of said inter-looped distal end portions from said wire mesh distal end has a magnitude in a range of between 0.2 mm and 1.5 mm.

14. The external support of claim 1, wherein said wire mesh distal portion has all said paired plastically deformable wires configured such that said first and second wire closed loops of said inter-looped distal end portions radially extend beyond the outer radius of said wire mesh.

15. The external support of claim 14, wherein said apexes of all said inter-looped distal end portions are outwardly radially offset from, and not coincident with, the outer circumferential periphery of said wire mesh.

16. The external support of claim 15, wherein said outward radial offset of each one of said apexes of said inter-looped distal end portions out or outwardly from said wire mesh outer circumferential periphery has a magnitude in a range of between 0.2 mm and 1.5 mm.

17. The external support of claim 1, wherein, within said wire mesh middle portion, structural geometrical and mechanical features, properties, and characteristics of said non-paired elastic wires and of said paired plastically deformable wires are spatially, longitudinally and radially symmetric and uniform.

18. The external support of claim 1, wherein said non-paired elastic wires are constructed from materials being cold worked metals, or cold worked metal alloys, characterized by exhibiting elasticity, being elastic, and having elastic properties.

19. The external support of claim 1, wherein said paired plastically deformable wires are constructed from materials being hot worked or annealed metals, or, hot worked or annealed metal alloys, characterized by exhibiting plasticity, being plastically deformable, and having plastically deformable properties.

20. The external support of claim 1, wherein said wire mesh is configured with a total number of said elastic wires in a range of between 20 and 124, and with a total number of said plastically deformable wires in a range of between 4 and 32.

* * * * *